United States Patent
Christensen et al.

(10) Patent No.: US 12,203,911 B1
(45) Date of Patent: Jan. 21, 2025

(54) SENSOR DISCRIMINATORS AND METHODS FOR DETECTING ELECTRICAL PROPERTY CHANGES IN A METAL ORGANIC FRAMEWORK

(71) Applicants: Honeywell Federal Manufacturing & Technologies, LLC, Kansas City, MO (US); National Technology and Engineering Solutions of Sandia, LLC, Albuquerque, NM (US)

(72) Inventors: Daniel A. Christensen, Kansas City, MO (US); Ratthatrust Leryoskajai, Kansas City, MO (US); Nathan S. L. Volkmann, Lee's Summit, MO (US); Mara Elizabeth Schindelholz, Columbus, OH (US); Leo J. Small, Albuquerque, NM (US); Tina M. Nenoff, Albuquerque, NM (US); Stephen J. Percival, Albuquerque, NM (US)

(73) Assignees: Honeywell Federal Manufacturing & Technologies, LLC, Kansas City, MO (US); National Technology and Engineering Solutions of Sandia, LLC, Albuquerque, NM (US)

( * ) Notice: Subject to any disclaimer, the term of this patent is extended or adjusted under 35 U.S.C. 154(b) by 0 days.

(21) Appl. No.: 18/237,798

(22) Filed: Aug. 24, 2023

Related U.S. Application Data

(62) Division of application No. 17/990,144, filed on Nov. 18, 2022, now Pat. No. 11,867,677.

(51) Int. Cl.
*G01N 33/00* (2006.01)
*B01J 20/22* (2006.01)

(52) U.S. Cl.
CPC ......... *G01N 33/0034* (2013.01); *B01J 20/226* (2013.01)

(58) Field of Classification Search
None
See application file for complete search history.

(56) References Cited

U.S. PATENT DOCUMENTS

| 2015/0253300 A1* | 9/2015 | Zanfei | G01N 33/0075 702/24 |
|---|---|---|---|
| 2021/0285907 A1 | 9/2021 | Makaram et al. | |

(Continued)

OTHER PUBLICATIONS

U.S. Appl. No. 18/532,674 Non-Final Office Action issued Jul. 22, 2024.

*Primary Examiner* — Daniel S Larkin
(74) *Attorney, Agent, or Firm* — Erise IP, P.A.

(57) ABSTRACT

A sensor discriminator for detecting a gaseous substance includes a power source, a discrimination module, a sensor simulator that simulates a metal organic framework under at least one simulation condition, a simulation circuitry electrically coupling the sensor simulator to the power source and the discrimination module, and a discriminator circuitry that electrically couples the power source and the discrimination module to a gas capture probe. The discrimination module compares a discrimination pulse and a simulation pulse from the power source after the discrimination pulse passes through a metal organic framework of the gas capture sensor and the simulation pulse passes through a simulation component of the sensor simulator. The discrimination module causes a discriminator output that includes the comparison of the discrimination pulse to the simulation pulse. An electrical property of the discrimination pulse depends on an electrical parameter of the metal organic framework that is augmented by the gaseous substance.

7 Claims, 9 Drawing Sheets

(56) References Cited

U.S. PATENT DOCUMENTS

Figure 1:
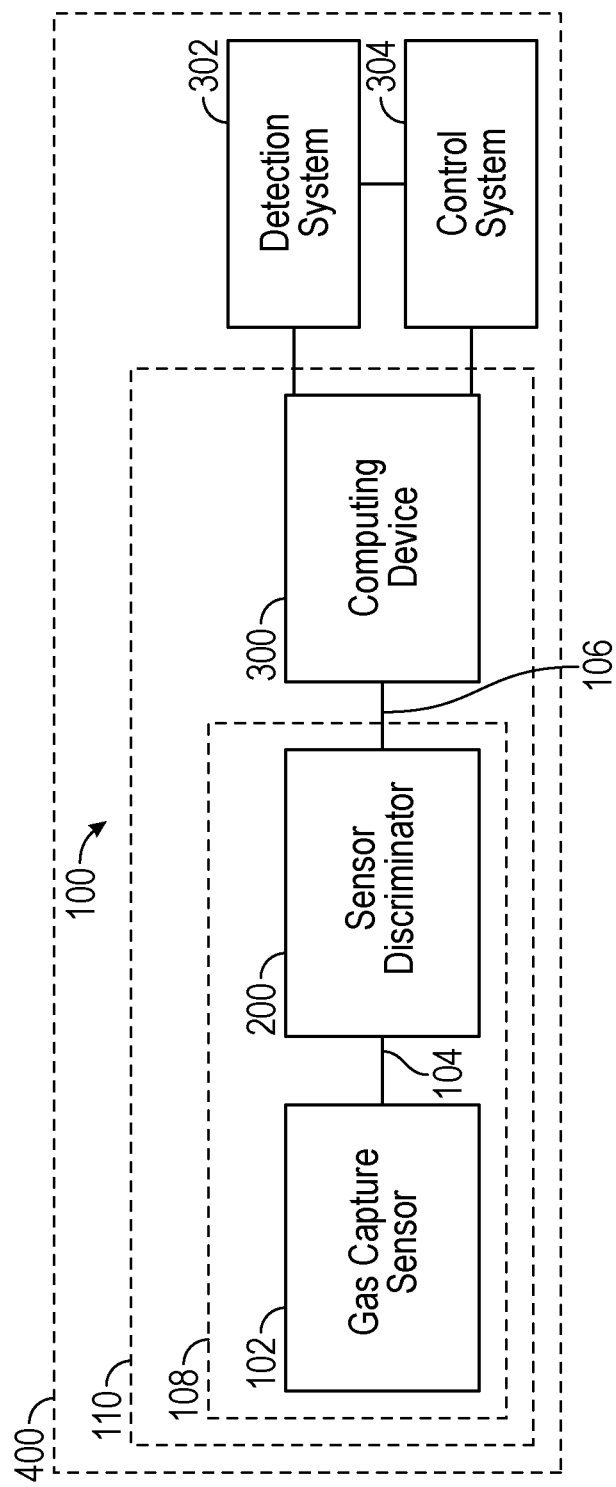

2022/0082525 A1 3/2022 Britt et al.
2022/0260541 A1 8/2022 Small et al.

* cited by examiner

SENSOR DISCRIMINATORS AND METHODS FOR DETECTING ELECTRICAL PROPERTY CHANGES IN A METAL ORGANIC FRAMEWORK

RELATED APPLICATION

The present application is a divisional application claiming priority benefit, with regard to all common subject matter, of similarly titled U.S. patent application Ser. No. 17/990,144, filed Nov. 18, 2022, now U.S. Pat. No. 11,867, 677. The above-referenced patent application is hereby incorporated by reference in its entirety into the present application.

STATEMENT OF GOVERNMENT SUPPORT

This invention was made with government support under contract number DE-NA0002839 awarded by the United States Department of Energy/National Nuclear Security Administration. The government has certain rights in the invention.

FIELD

The present disclosure generally pertains to systems, apparatuses, and methods for detecting electrical property changes in a sensor.

BACKGROUND

Metal organic frameworks (MOFs) have been developed that exhibit a change in one or more electrical properties when exposed to various gaseous substances. Some of these gaseous substances may have environmental and/or health impacts. Gaseous substances may be emitted from known sources, such as combustion systems, point sources, or area sources. Gaseous substances may also be emitted from unknown sources, such as sources within a monitoring area. The emission of gaseous substances may occur continuously or intermittently, and/or regularly or unexpectedly. The presence or concentration of gaseous substances may vary from time-to-time. The presence or concentration of gaseous substances may be of interest at low concentrations, such as on the order of parts-per-million (ppm) Recognizing the change in one or more electrical properties exhibited by MOFs when exposed to a gaseous substance, there remains a need for systems, apparatuses, and methods of detecting various gaseous substances corresponding to changes in electrical properties of MOFs under various conditions.

SUMMARY

Aspects, features, and advantages of the presently disclosed subject matter are set forth in part in the following description. Further aspects and advantages may be apparent from the description or through practicing the presently disclosed subject matter.

In one aspect, the present disclosure provides sensor discriminators for detecting at least one gaseous substance based on a change in at least on electrical property of a metal organic framework when exposed to at least one gaseous substance. In at least on example, a sensor discriminator may include a power source, a discrimination module, a sensor simulator that includes at least one simulation component configured to simulate a metal organic framework under at least one simulation condition, a simulation circuitry electrically coupling the sensor simulator to the power source and the discrimination module, and a discriminator circuitry configured to electrically couple the power source and the discrimination module to a gas capture sensor comprising the metal organic framework.

The discrimination module may include a comparator configured to perform a comparison of a discrimination pulse to a simulation pulse in respect of at least one electrical property. The discrimination pulse may include a first electrical pulse from the power source having passed through the metal organic framework of the gas capture probe, and the simulation pulse may include a second electrical pulse from the power source having passed through the at least one simulation component of the sensor simulator. The discrimination module may be configured to cause a discriminator output that includes the comparison of the discrimination pulse to the simulation pulse. The at least one electrical property may depend at least in part on at least one electrical parameter of the metal organic framework. The at least one electrical parameter of the metal organic framework may be augmented by a presence and/or a concentration of the at least one gaseous substance, and the discriminator output indicative of the presence and/or the concentration of the at least one gaseous substance.

In at least one example, a sensor discriminator, may include a sensor simulator having at least one simulation component configured to simulate a metal organic framework under at least one simulation condition, a simulation circuitry electrically coupled to the sensor simulator, a discriminator circuitry electrically coupled the metal organic framework, and a comparator configured to perform a comparison of a discrimination pulse to a simulation pulse in respect of at least one electrical property. The discrimination pulse may include a first electrical pulse having passed through the metal organic framework. The simulation pulse may include a second electrical pulse having passed through the at least one simulation component of the sensor simulator. The comparator may be configured to cause a discriminator output that includes the comparison of the discrimination pulse to the simulation pulse.

In yet another aspect, the present disclosure provides methods of monitoring a gaseous substance. A method may include determining a discrimination pulse, determining a simulation pulse, and causing a discriminator output indicative of the presence and/or the concentration of the gaseous substance. The discrimination pulse may include a first electrical pulse from a power source having passed through a gas capture sensor comprising a metal organic framework. The metal organic framework may include at least one electrical property that is dependent at least in part on a presence and/or a concentration of the gaseous substance. The metal organic framework may augment the discrimination pulse based at least in part on the at least one electrical property. The simulation pulse may include a second electrical pulse from the power source having passed through a sensor simulator that includes at least one simulation component configured to simulate the metal organic framework under at least one simulation condition. The discriminator output may include a comparison of the discrimination pulse and the simulation pulse in respect of at least one electrical property.

These and other aspects, features, and advantages thereof are further understood with reference to the following description, the accompanying drawing figures, and the appended claims. The foregoing summary is not intended to identify key features or essential features of the claimed subject matter, nor is it intended to limit the scope of the claimed subject matter.

BRIEF DESCRIPTION OF THE DRAWING FIGURES

Figure 2:
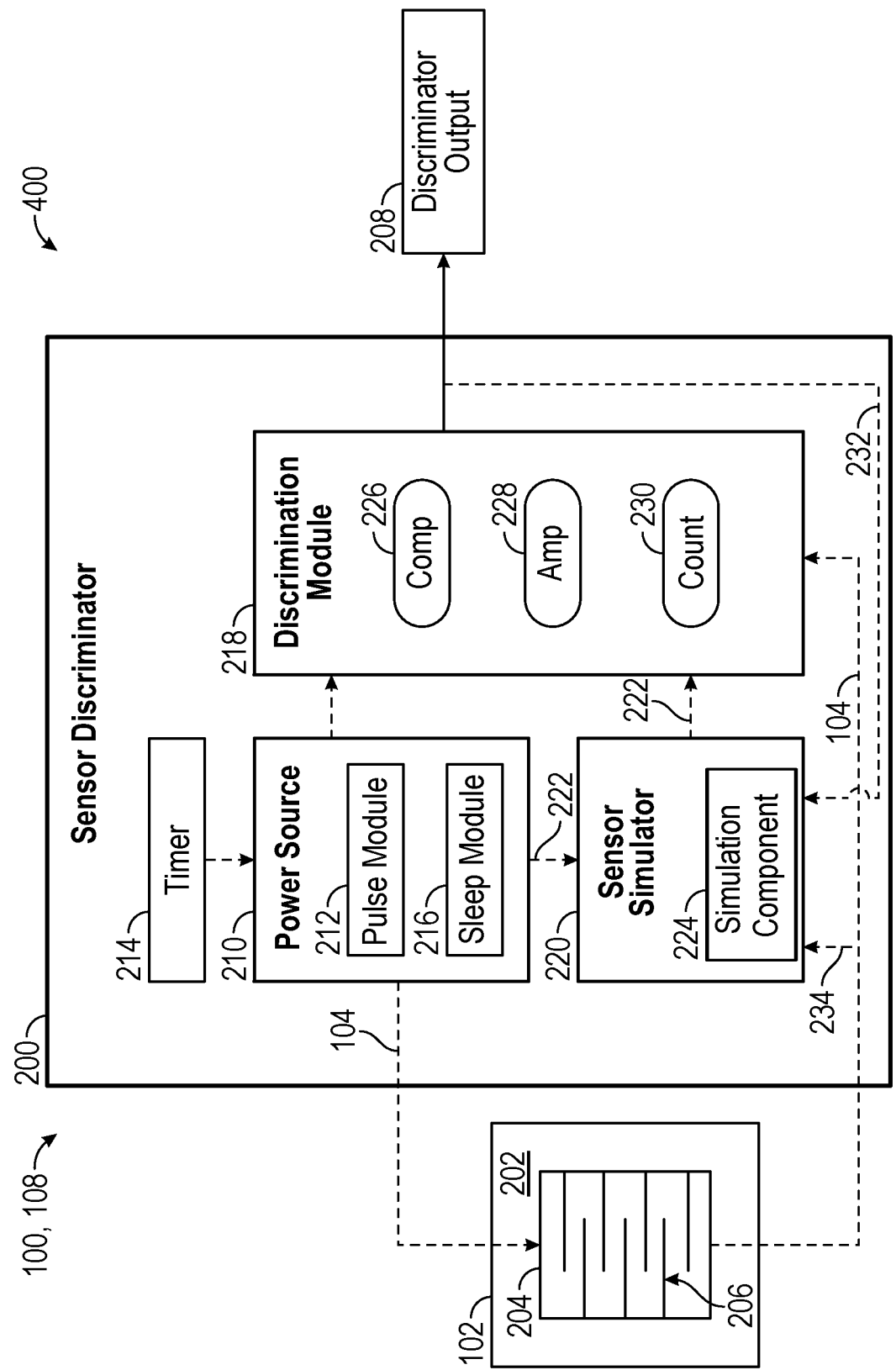
Figure 3:
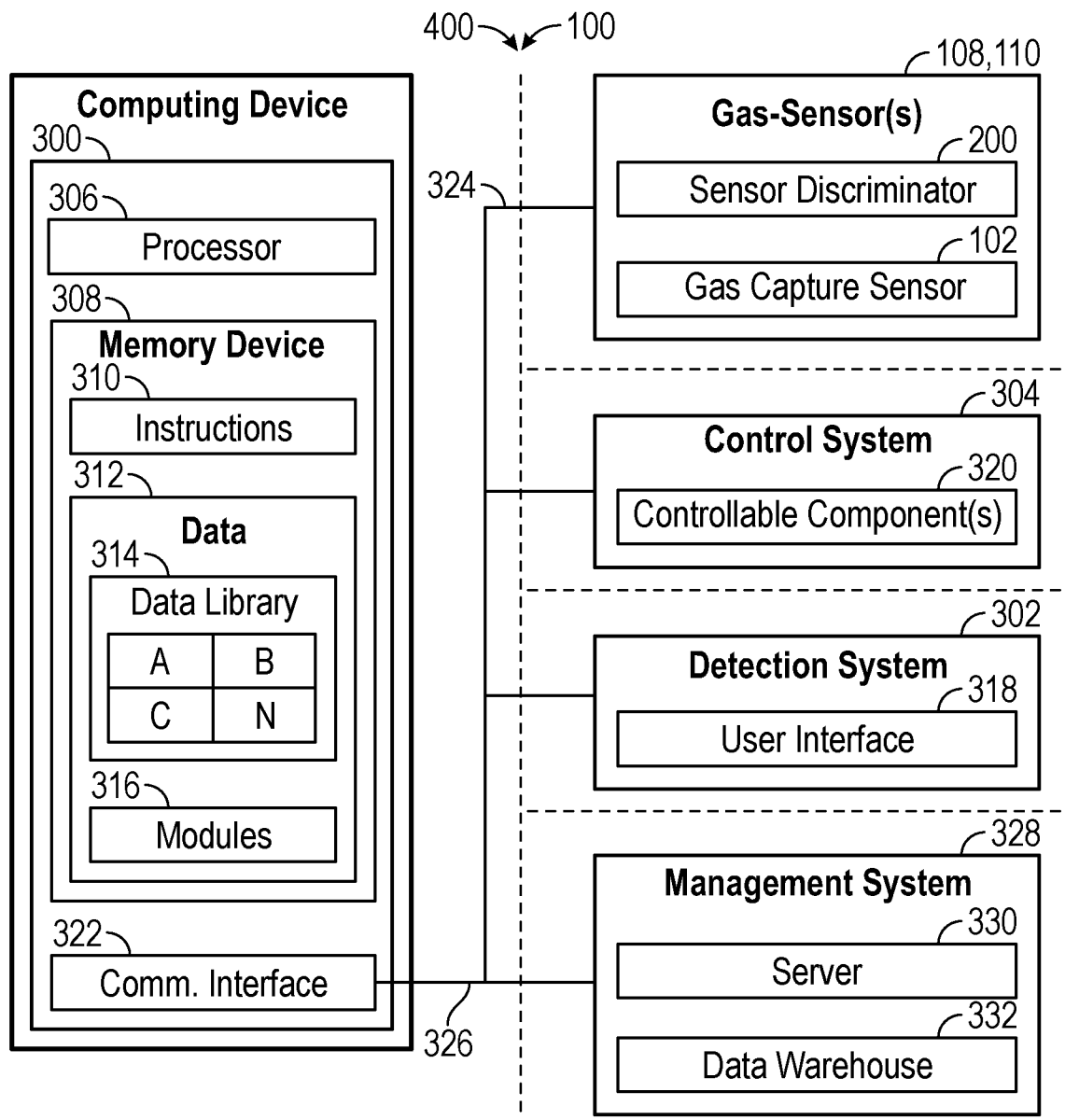
Figure 4A:
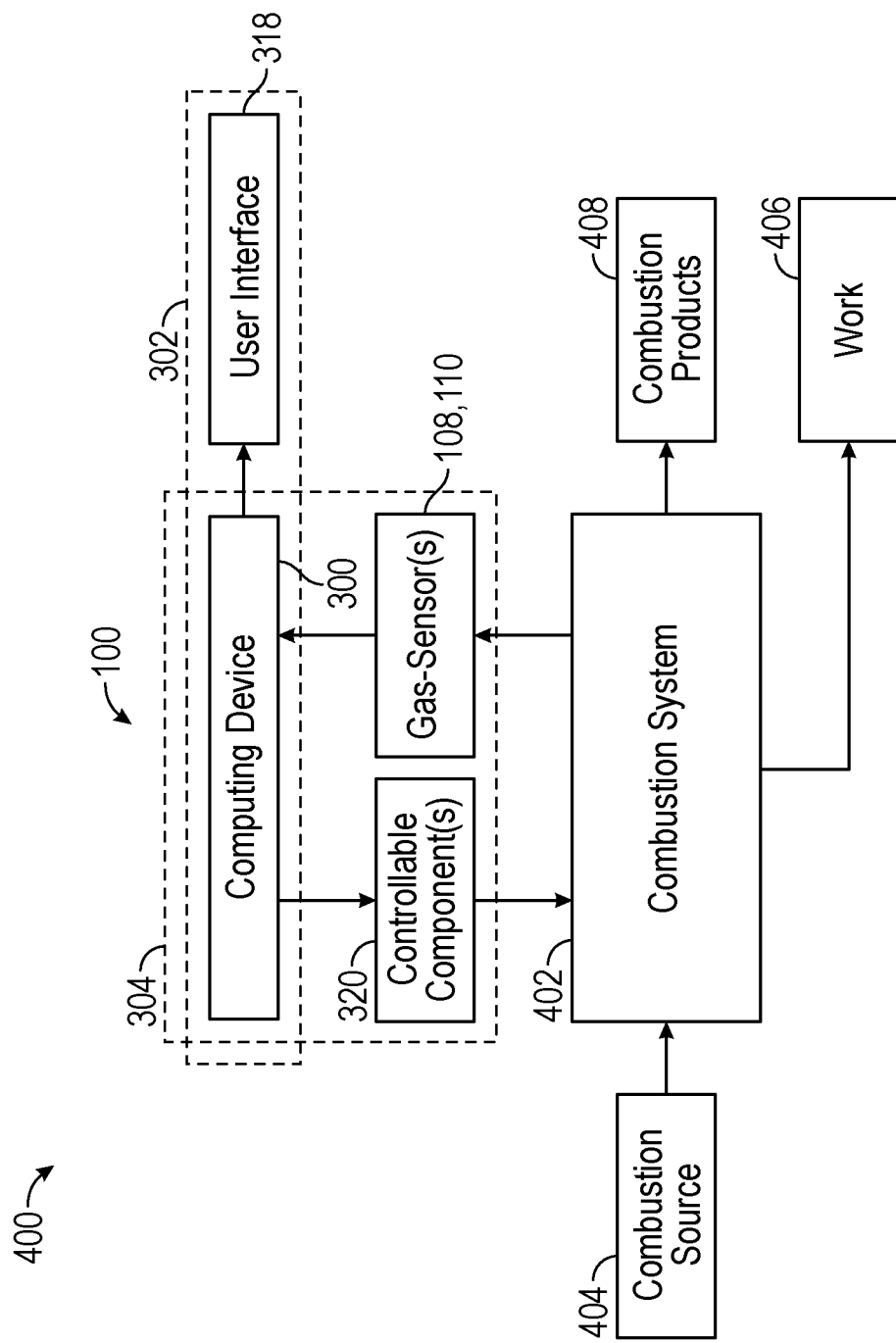
Figure 4B:
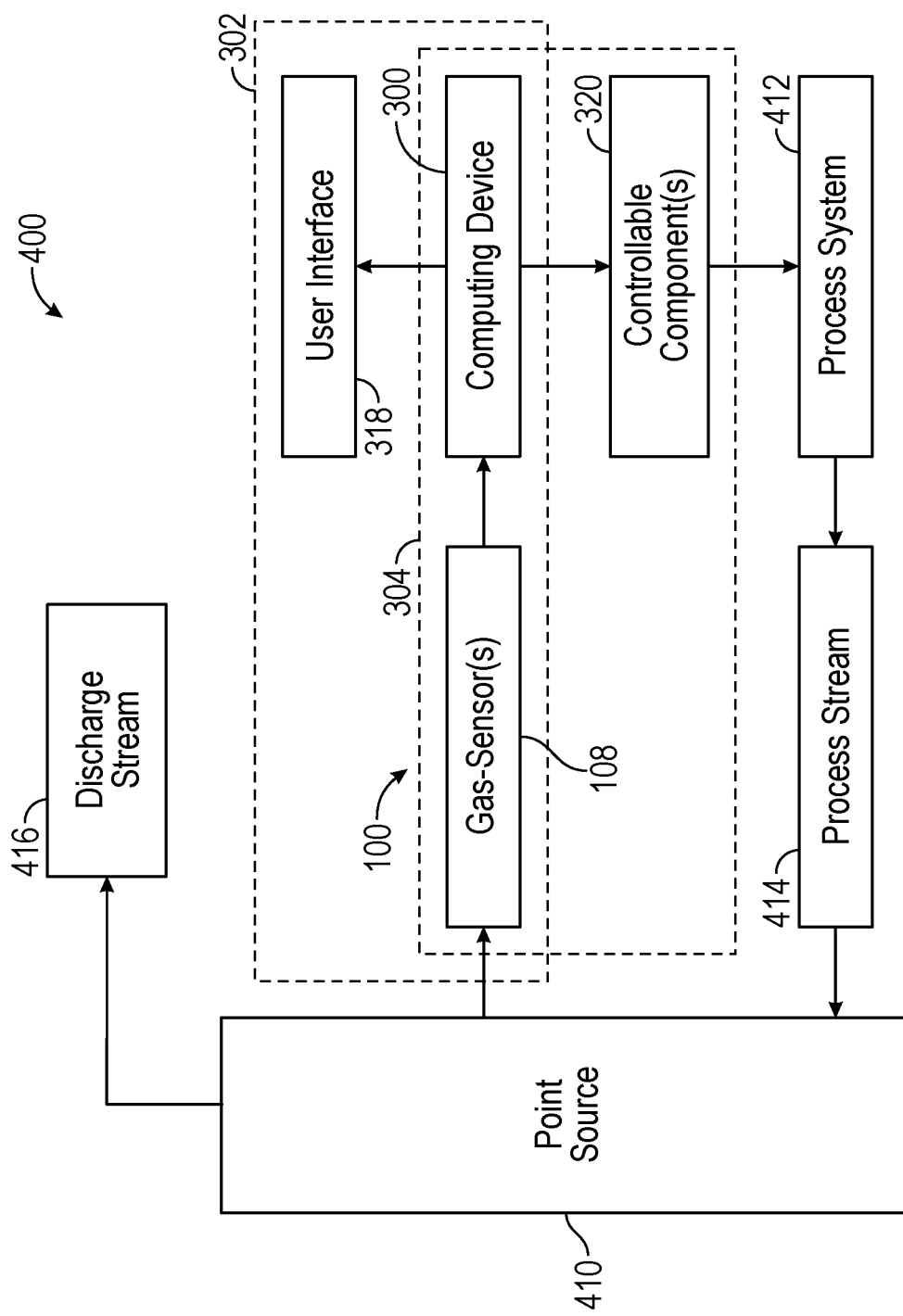
Figure 4C:
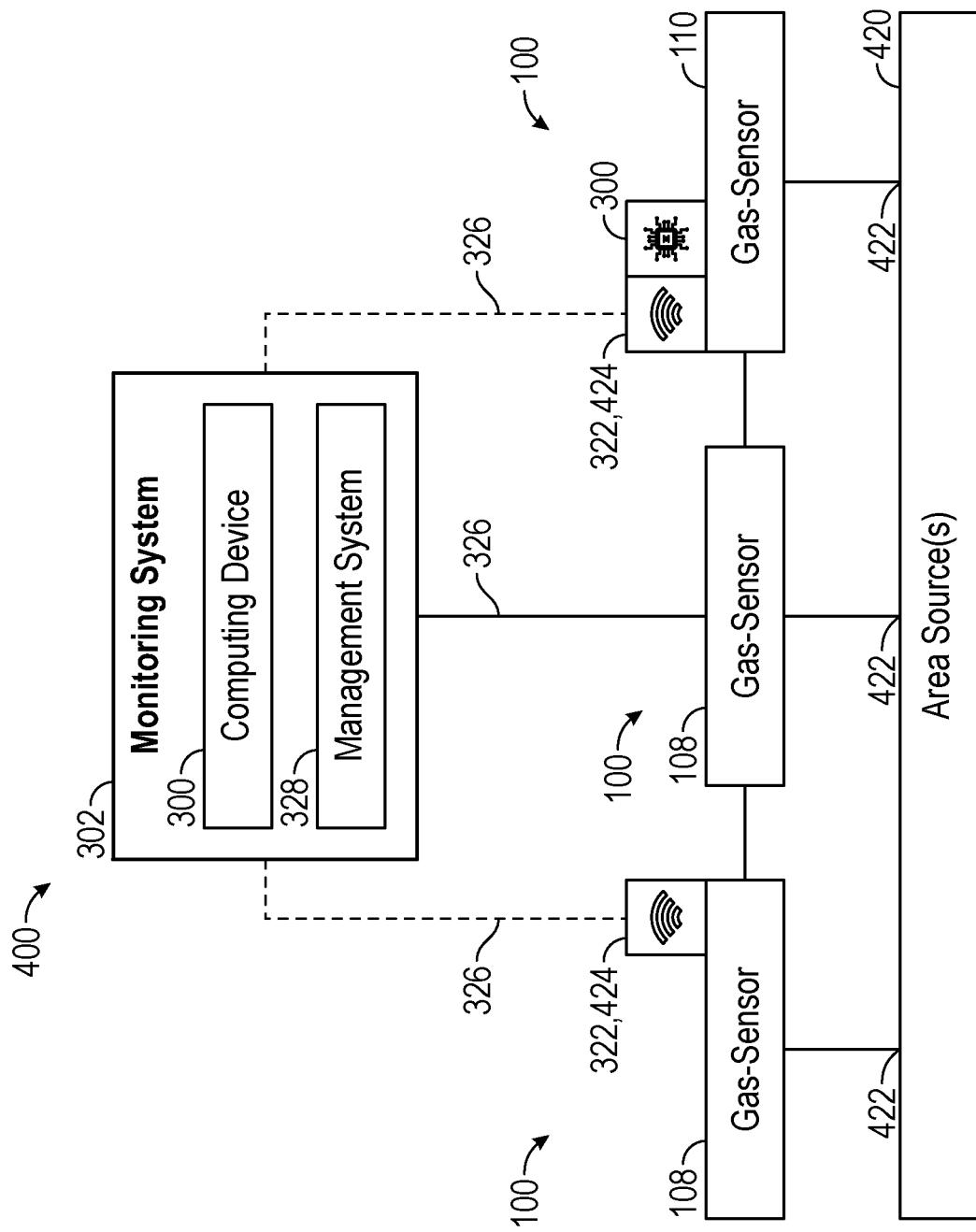
Figure 4D:
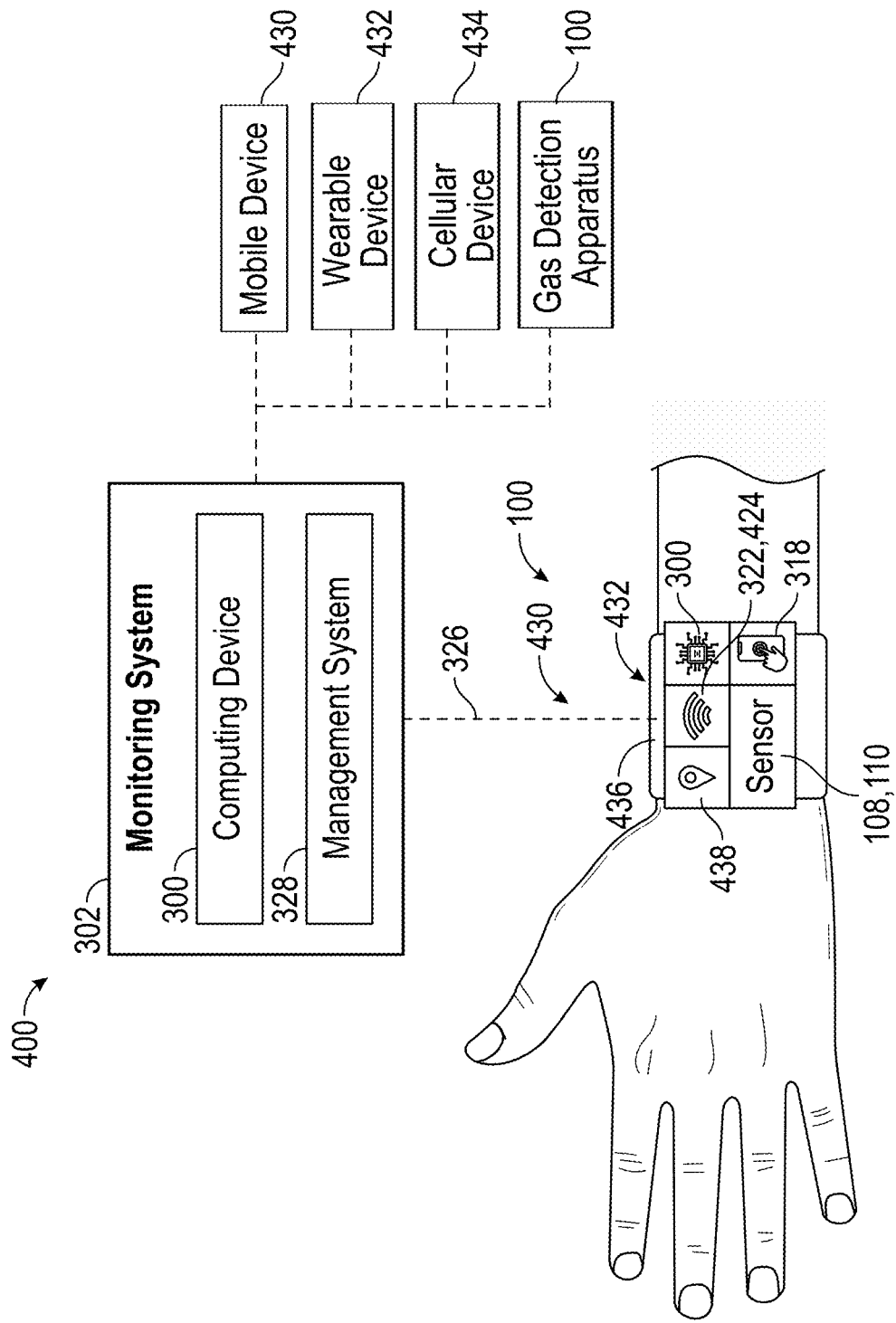
Figure 4E:
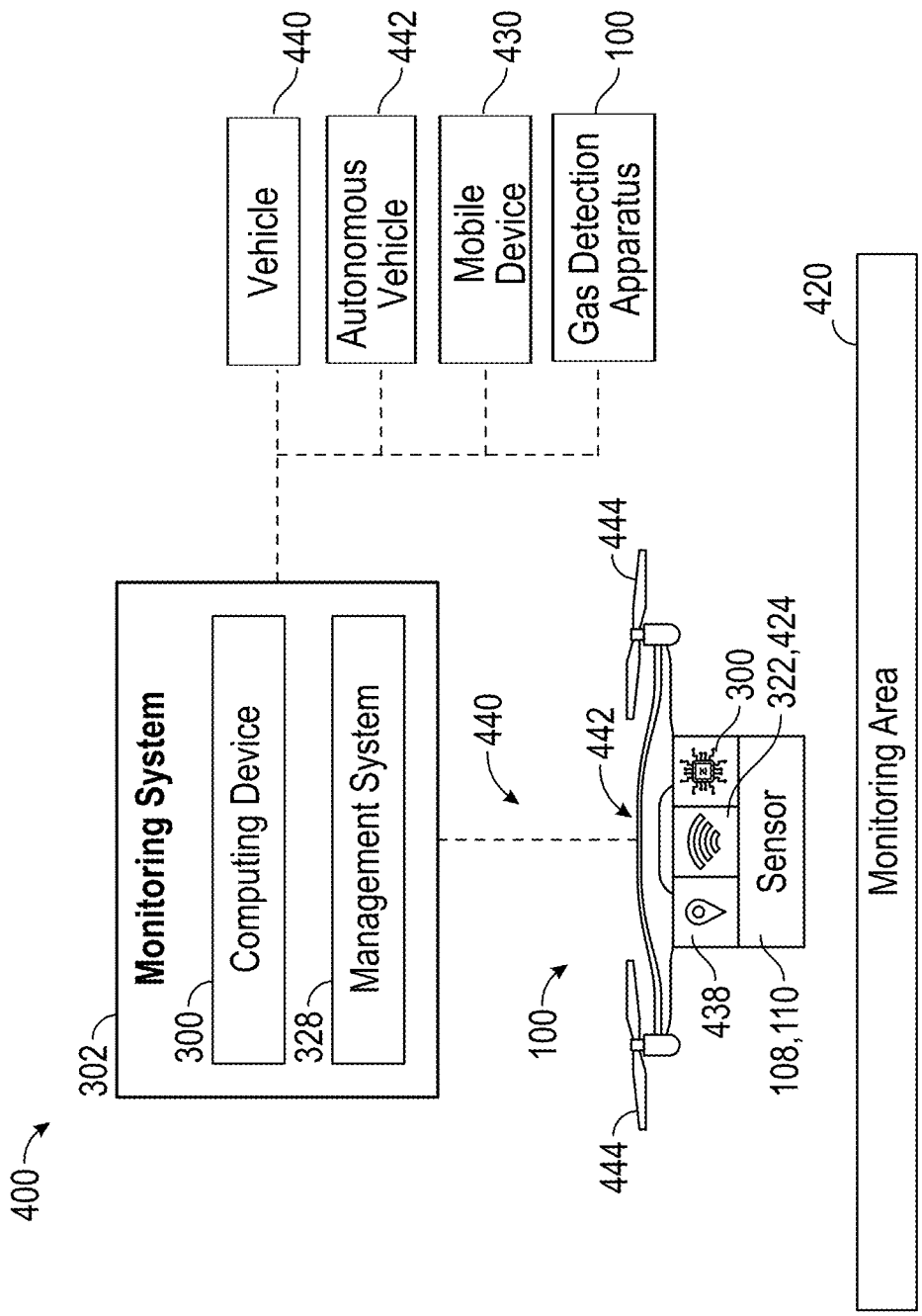
Figure 5:
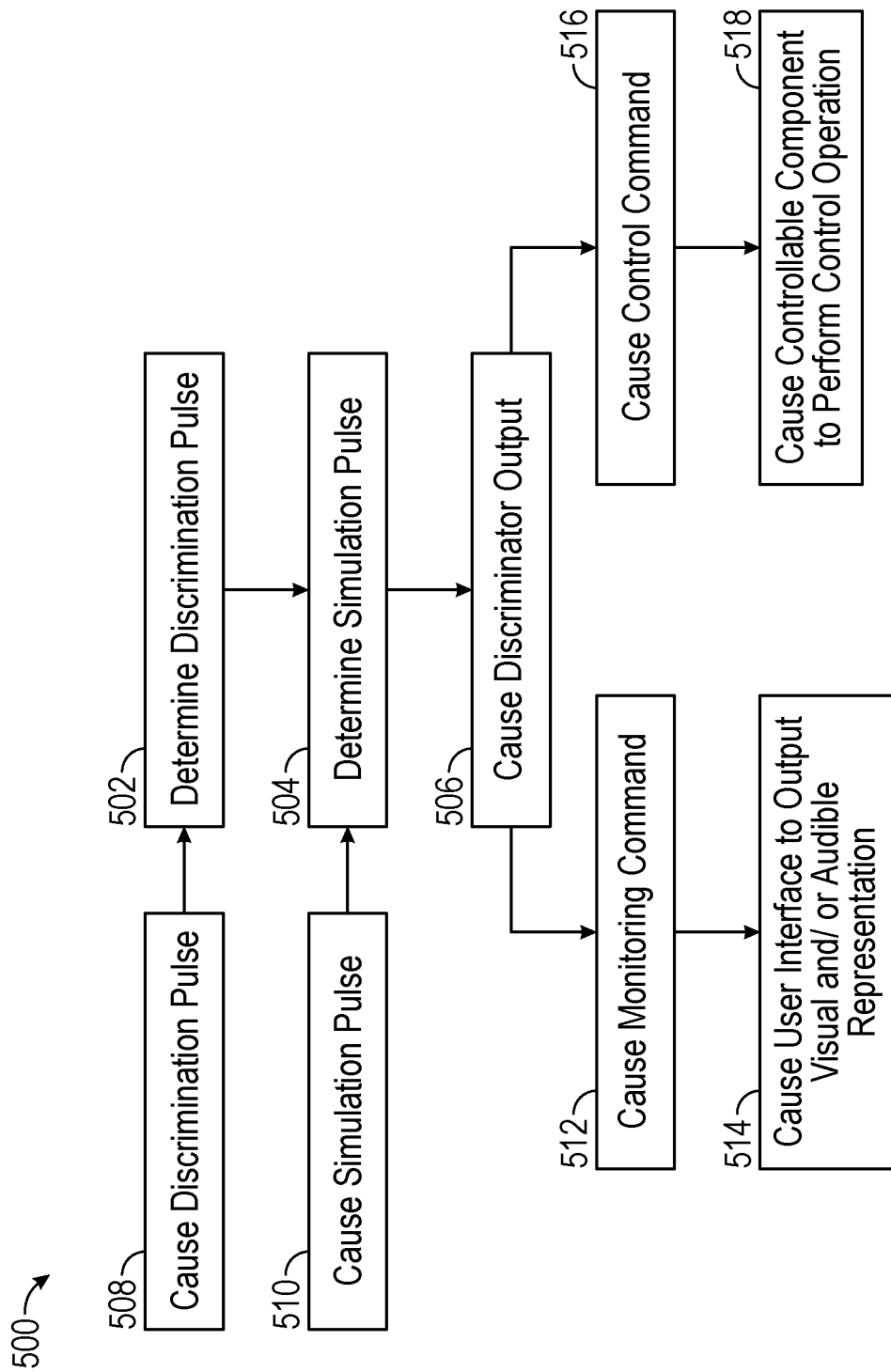

Embodiments of the present are described in detail below with reference to the attached drawing figures, wherein:

FIG. 1 schematically depicts an example of a gas detection apparatus;

FIG. 2 schematically depicts an example of a sensor discriminator;

FIG. 3 schematically depicts an example of a gas detection system;

FIG. 4A schematically depicts an example of a gas detection system implemented in association with a combustion system;

FIG. 4B schematically depicts an example of a gas detection system implemented in association with a point source;

FIG. 4C schematically depicts an example of a gas detection system implemented in association with an area source;

FIG. 4D schematically depicts an example of a gas detection system implemented in association with a mobile device;

FIG. 4E schematically depicts an example of a gas detection system implemented in association with a vehicle; and FIG. 5 schematically depicts an example method of detecting a gaseous substance.

The drawing figures illustrate example embodiments of the presently disclosed subject matter. The claims are not limited to the example embodiments depicted in the drawing figures. The aspects and features depicted in the drawing figures are not necessarily to scale. Repeat use of reference characters in the specification and drawing figures represent the same or analogous aspects or features.

DETAILED DESCRIPTION

The following detailed description references the accompanying drawing figures that illustrate example embodiments of the presently disclosed subject matter. The present disclosure, including the example embodiments depicted in the drawing figures, describe features, aspects, and advantages of the of the disclosed subject matter by way of explanation and not limitation. Various modifications, combinations, and variations can be made to the example embodiments or to aspects or features thereof without departing from the scope of the presently disclosed subject matter. Thus, the present disclosure encompasses such modifications, combinations, and variations. The present disclosure provides sufficient detail to enable those skilled in the art to practice the claimed subject matter. The present disclosure is, therefore, not to be taken in a limiting sense. The scope of the invention is defined only by the appended claims, along with the full scope of equivalents to which such claims are entitled.

In this description, references to "one embodiment," "an embodiment," or "embodiments" mean that the feature or features referred to are included in at least one embodiment of the presently disclosed subject matter. Separate references to "one embodiment," "an embodiment," or "embodiments" in this description do not necessarily refer to the same embodiment and are also not mutually exclusive unless so stated and/or except as will be readily apparent to those skilled in the art from the description. For example, a feature, structure, act, etc. described in one embodiment may also be included in other embodiments but is not necessarily included. Thus, the scope of the presently disclosed subject matter encompasses a variety of combinations and/or integrations of the example embodiments in this description.

The terms "a," "an," and "the" do not denote a limitation of quantity but rather denote the presence of at least one of the referenced item. The terms "first," "second," "third," and so forth may be used interchangeably to distinguish one item from another and are not intended to signify location or importance of the respective item. Range limitations in this description and in the claims include all endpoints, and all such endpoints are independently combinable to provide another range limitation.

The term "coupled," when used herein with reference to at least two objects, refers to direct or indirect mechanical or physical contact between two objects in which the two objects are linked, connected, fastened, or joined with one another, including by way of an interference fit, one or more fastening elements or hardware, by adhesive, by bonding, by welding, or the like. The term "coupled" includes objects that are removably coupled with one another as well as objects that are permanently coupled to one another.

The term "integral" or "integrally formed," when used herein with reference to at least to elements, refers to two elements that respectively define a portion, part, or piece of one and the same object, and/or two objects that are permanently coupled to one another such that the objects cannot be separated from one another without destructive means. The term "integral" includes a portion, part, or piece of an element that cannot be separated from the whole of the element without destructive means. For example, the term "integral" may refer to objects that are welded together, objects that are formed or cast as a single unit, as well as portions, parts, or pieces of a single, monolithic object.

The present disclosure provides gaseous substance detection systems and apparatuses, and methods of detecting a gaseous substance. The presently disclosed gaseous substance detection systems and apparatuses utilize a sensor discriminator configured to provide a discriminator output indicative of a presence and/or a concentration of at least one gaseous substance. The sensor discriminator provides electrical pulses that pass through a gas capture sensor that includes a metal organic framework (sometimes referred to herein as an "MOF"). The MOF may be capable of adsorbing, such as preferentially adsorbing, a gaseous substance of interest. The adsorption of the gaseous substance augments at least one electrical property of the MOF. The electrical pulses that pass through the gas capture sensor may have at least one electrical parameter that depends at least in part on the at least one electrical property of the MOF. The sensor discriminator may provide an output that includes and/or that is based at least in part on the at least one electrical property of the electrical pulses that pass through the gas capture probe.

The sensor discriminator may include a sensor simulator that simulates at least one electrical property of the MOF under at least one simulation condition. The at least one simulation condition may include a simulation of the MOF prior to having adsorbed the gaseous substance of interest. The sensor simulator may include at least one simulation components that simulate the at least one electoral property of the MOF under the simulation conditions The sensor discriminator may provide electrical pulses that pass through the sensor simulator. The sensor discriminator may compare the electrical pulses that pass through the gas capture sensor to the electrical pulses that pass through the sensor simulator, and the sensor discriminator may provide a discriminator output based at least in part on the comparison of the electrical pulses. The discriminator output may be indicative of a presence and/or a concentration of the gaseous substance of interest.

The presently disclosed sensor discriminators and/or gas capture sensors may be included in a gas detection apparatus, such as a gas-sensor or a smart gas-sensor. A gaseous substance detection systems may include one or more gas detection apparatuses. By way of example, and without limitation, a gaseous substance detection system may be implemented in association with a combustion system, a point source, an area source, a mobile device, or a vehicle, as well as combinations of these. The gaseous substance detection system may include a monitoring system and/or a control system.

These and other features of the presently disclosed subject matter are described with reference to the Figures.

Referring now to the Figures, the presently disclosed subject matter is further described. As shown in FIG. 1, a gas detection apparatus 100 may include at least one sensor discriminator 200. A sensor discriminator 200 may be configured to provide a discriminator output indicative of a presence and/or a concentration of at least one gaseous substance. The discriminator output may include and/or may be based on at least one electrical property of a gas capture sensor 102. The at least one electrical property of the gas capture sensor 102 may be indicative of the presence and/or the concentration of at least one gaseous substance. The at least one electrical property of the gas capture sensor 102 may be augmented by, and/or may depend at least in part on, the presence and/or the concentration of the at least one gaseous substance. The presence and/or the concentration of the at least one gaseous substance may be determined based at least in part on the at least one electrical property of the gas capture sensor 102, for example, as indicated by the discriminator output.

In some embodiments, a gas detection apparatus 100 may include at least one gas capture sensor 102. The at least one gas capture sensor 102 may be electrically couplable or coupled to the at least one sensor discriminator 200, for example, via a discriminator circuitry 104. A gas capture sensor 102 may define a portion of the gas detection apparatus 100. Additionally, or in the alternative, a gas capture sensor 102 may be provided as a separate component or apparatus, and the gas detection apparatus 100 may be electrically and/or communicatively coupled to the gas capture sensor 102.

In some embodiments, a gas detection apparatus 100 may define a portion of a gas detection system 400. A gas detection system 400 includes at least one gas detection apparatus 100. In some embodiments, a gas detection system 400 may include a plurality of gas detection apparatuses 100. A gas detection apparatus 100 and/or a gas detection system 400 may include at least one computing device 300. In some embodiments, a gas detection apparatus 100 may include a computing device 300 electrically and/or communicatively couplable or coupled to the at least one sensor discriminator 200, for example, via computing circuitry 106. The computing device 300 may define a portion of the sensor discriminator 200, or the sensor discriminator 200 may define a portion of the computing device 300. Alternatively, the sensor discriminator 200 and the computing device 300 may define respectively separate components of the gas detection apparatus 100. Additionally, or in the alternative, the gas detection system 400 may include a computing device 300 communicatively couplable or coupled to a gas detection apparatus 100, such as via wired or wireless communication links. The at least one computing device 300 may be configured to determine a presence and/or a concentration of at least one gaseous substance based at least in part on discriminator outputs from the sensor discriminator 200. Additionally, or in the alternative, the at least one computing device 300 may be configured to store the discriminator outputs for further processing or use. Additionally, or in the alternative, the at least one computing device 300 may be configured to generate and/or store data based least in part on the discriminator outputs.

In some embodiments, the gas detection system 400 may include a monitoring system 302. One or more gas detection apparatuses 100 may include and/or may be communicatively coupled to the monitoring system 302. The monitoring system 302 may include and/or may utilize the at least one computing device 300 to monitor at least one gas detection apparatus 100. The monitoring system 302 may include one or more components communicatively coupled to the at least one computing device 300. The monitoring system 302 may be configured to monitor and/or process discriminator outputs 208 and/or data from the at least one gas detection apparatus 100. The discriminator outputs and/or data from the at least one gas detection apparatus 100 may be monitored and/or processed, for example, to determine a presence and/or a concentration of at least one gaseous substance and/or to determine further information associated with the presence and/or the concentration of the at least one gaseous substance. The monitoring system 302 may provide monitoring commands, such as to a user interface, based at least in part on discriminator outputs. The monitoring commands may be configured to cause the user interface to provide a visual or audible representation indicative of the presence and/or the concentration of the at least one gaseous substance.

In addition, or in the alternative to a monitoring system 302, a gas detection system 400 and/or a gas detection apparatus 100 may include and/or may be communicatively coupled to a control system 304. One or more gas detection apparatuses 100 may include and/or may be communicatively coupled to the control system 304. The control system 304 may include and/or may utilize the at least one computing device 300. The control system 304 may include one or more components communicatively coupled to the at least one computing device 300. The control system 304 may be communicatively coupled to the monitoring system 302. Additionally, or in the alternative, the control system 304 may define a portion of the monitoring system 302, or the monitoring system 302 may define a portion of the control system 304. The control system 304 may be configured to provide control commands to at least one controllable component responsive a determination of a presence and/or a concentration of at least one gaseous substance. The control commands may be provided responsive to discriminator outputs indicative of the presence and/or the concentration of the at least one gaseous substance. Additionally, or in the alternative, the control commands may be provided responsive to data generated and/or stored based least in part on the discriminator outputs. In some embodiments, at least one controllable component may be configured to control at least one process parameter associated with the gas detection system 400, such as at least one process parameter of a system or apparatus associated with a formation, presence, remediation, and/or concentration of the at least one gaseous substance.

A gas detection apparatus 100 that includes a sensor discriminator 200 electrically and/or communicatively couplable or coupled to at least one gas capture sensor 102 may sometimes be referred to as a gas-sensor 108. In some embodiments, a gas capture sensor 102 may define a component of the gas-sensor 108. A gas-sensor 108 that includes a sensor discriminator 200 and a computing device 300 may sometimes be referred to as a smart gas-sensor 110. The term "gas-sensor" is inclusive of the term "smart gas-sensor" unless the context requires otherwise. A gas detection system 400 may include at least one gas-sensor 108 and/or at least one smart gas-sensor 110. In some embodiments, at least one gas-sensor 108 may be communicatively coupled to at least one smart gas-sensor 110.

In some embodiments a gas capture sensor 102 may define at least part of a component or apparatus separate from, yet couplable to, a gas-sensor 108. A gas capture sensor 102 may be interchangeably couplable or coupled to a gas-sensor 108, such as to the sensor discriminator 200 and/or to the discriminator circuitry 104 of the gas-sensor 108. In some embodiments, the gas capture sensor 102 may be replaced from time-to-time, such as for maintenance or repair purposes. Additionally, or in the alternative, the gas capture sensor 102 may be selected and/or interchanged according to the at least one gaseous substance detectable or to be detected by the gas detection apparatus 100. In some embodiments, a gas-sensor 108 may include, or may be electrically and/or communicatively couplable or coupled to, a plurality of gas capture sensors 102. The plurality of gas capture sensors 102 may respectively correspond to a respective one of a plurality of gaseous substances that the gas detection apparatus 100 may be configured to detect. Additionally, or in the alternative, the plurality of gas capture sensors 102 may respectively correspond to a respective one of a plurality of concentration ranges or levels of a gaseous substances that the gas detection apparatus 100 may be configured to detect. In some embodiments, a gas-sensor 108 may include a sensor discriminator 200 configured to provide discriminator outputs indicative of a presence and/or a concentration of the respective ones of the plurality of gaseous substances and/or concentration ranges or levels. Additionally, or in the alternative, a gas-sensor may include a plurality of sensor discriminators 200 respectively corresponding to a respective one of a plurality of gas capture sensors 102.

Referring now to FIG. 2, example gas detection apparatuses 100 and/or example gas-sensors 108 are further described. As shown, a detection apparatuses 100 and/or a gas-sensor 108 may include a gas capture sensor 102 and a sensor discriminator 200. The gas capture sensor 102 may include a substrate 202, a metal organic framework 204 (MOF) disposed about the substrate 202, and an electrode array 206 disposed within and/or at least partially surrounded by the MOF 204. The substrate 202 may include a glass, a plastic, or the like. The electrode array 206 may include an interdigitated electrode array, a ring electrode array, or the like. The MOF 204 and the electrode array 206 define a portion of the discriminator circuitry 104.

The sensor discriminator 200 may be configured to provide a discriminator output 208 that depends at least in part on one or more electrical properties of the MOF 204, such as resistance, capacitance, or impedance of the MOF 204. The discriminator output 208 may include one or more electrical parameters, such as voltage, amplitude, duration, polarity, frequency, and/or phase. The one or more electrical parameters of the discriminator output 208 may depend at least in part on the one or more electrical properties of the MOF 204.

As shown in FIG. 2, the sensor discriminator may include a power source 210 electrically coupled or couplable to the gas capture sensor 102, such as to the electrode array 206 of the gas capture sensor 102, via the discriminator circuitry 104. The power source 210 may provide a direct current (DC) output or an alternating current (AC) output. The power source 210 may operate at a power level of from 1 picowatt (pW) to 1,000 pW, such as from 1 pW to 15 pW, such as from 25 pW to 100 pW, such as from 100 pW to 500 pW, or such as from 500 pW to 1,000 pW. The power source 210 may provide a current of from 1 milliampere (mA) to 1,000 mA, such as from 1 mA to 10 mA, such as from 10 mA to 100 mA, or such as from 100 mA to 1,000 mA.

The power source 210 may include and/or may be electrically coupled to a pulse module 212 configured to cause the power source 210 to provide electrical pulses to the gas capture sensor 102 via the discriminator circuitry 104. The electrical pulses from the power source 210 may be provided periodically or intermittently, such as according to a pulse interval or a pulse prompt. The pulse interval may be determined by a timer 214 communicatively and/or electrically coupled to the power source 210 and/or the pulse module 212. The power source 210 may include a sleep module 216 configured to cause the power source 210 to enter a power-saving- or sleep-mode, for example, between electrical pulses. In some embodiments, a pulse interval and/or a pulse prompt may be provided by a computing device 300 (FIG. 1) communicatively coupled to the sensor discriminator 200. The computing device 300 may include and/or may be configured to control the pulse module 212, the timer 214, and/or the sleep module 216.

The power source 210 may provide electrical pulses, such as DC electrical pulses, that have an electrical potential of from 0.1 volt (V) to 10 V, such as from 0.1 V to 1 V, such as from 1 V to 5 V, or such as from 5 V to 10 V. Alternatively, the power source 210 may provide AC electrical pulses.

The power source 210 may provide electrical pulses, such as DC electrical pulses, at a pulse interval of less than 1 Hertz (Hz) to 25 Hz, such as from 1 micro-Hertz (mHz) to 100,000 mHz, such as from 1 mHz to 25 mHz, such as from 25 mHz to 50 mHz, such as from 50 mHz to 150 mHz, such as from 150 mHz to 250 mHz, such as from 250 mHz to 500 mHz, such as from 500 mHz to 1,000 mHz, such as from 1,000 mHz to 10,000 mHz, such as from 10,000 mHz to 25,000 mHz, such as from 25,000 mHz to 100,000 mHz, such as from 1 Hz to 10 Hz, or such as from 10 Hz to 20 Hz.

The power source 210 may provide electrical pulses that propagate through the MOF 204. An electrical pulse that propagates through the MOF 204 is sometimes referred to herein as a "discrimination pulse" or a "discrimination signal". At least one electrical parameter of the discrimination pulses (e.g., voltage, amplitude, duration, polarity, frequency, and/or phase) may be augmented based at least in part on the one or more electrical properties of the MOF 204.

One or more electrical properties of the MOF 204 (e.g., resistance, capacitance, inductance) may depend at least in part on a presence and/or a concentration of at least one gaseous substance adsorbed by the MOF 204. MOFs are a class of compounds that include metal ions coordinated to organic ligands. A MOF may have a one-, two-, or three-dimensional structure. The MOF may have a nanoporous structure capable of adsorbing one or more gaseous substances. In general, MOFs may be formed in the presence of a solvent, such as a volatile solvent, that can be subsequently removed (e.g., by heating or washing), thereby leaving exposed metal sites that that may preferentially adsorb a gaseous substance. A MOF may be selectively formed to preferentially adsorb at least one gaseous substance. MOFs are highly tunable due to the numerous combinations of metal and organic constituents. The respective combination of metal ions and organic constituents may provide different coordination geometries and/or may involve different chemical functionalities that may provide selective adsorption of one or more gaseous substances. A particular MOF may be selected for a gas capture sensor 102 based at least in part on its ability to selectively adsorb a gaseous substance of interest. As one example, a particularly suitable MOF may be selected from the family referred to as M-MOF-74 (also referred to as CPO-27 (M), where M includes at least one of the following divalent metallic cations: Zn, Mg, Mn, Co, Ni, Cu, Cd, or Fe. The MOF may include mono-metallic metal sites (e.g., M=Mn, Co, Ni, Zn), and/or multi-metallic metal sites (e.g., M=MnCo, MnNi, and MnZn) The M-MOF-74 family may provide a relatively high concentration of exposed metal sites.

A MOF 204 may be synthesized as a bulk material and may be dropcast onto the electrode array 206. For example, an M-MOF-74 material may be synthesized from a combination of one or more divalent metallic cations with the divergent organic ligand referred to as 2,5-dihydroxybenzene-1,4-dicarboxylate (DBDC). Other divalent metallic cations and/or other organic ligands may be selectively utilized, for example, to tune one or more properties of the MOF. Additionally, or in the alternative, post-synthetic modifications may be imparted to the structure of the MOF for example, to tune one or more properties of the MOF.

Further example MOFs include RE-DOBDC (where RE includes at least one of the following rare earth elements: yttrium, lanthanum, cerium, praseodymium, neodymium, promethium, samarium, europium, gadolinium, terbium, dysprosium, holmium, erbium, thulium, ytterbium, or lutetium; and DOBDC refers to 2,5-dihydroxyterephthalic acid), $[Zr_6O_4(OH)_4(FA)_6]_2(calixarene)_3$, MFM-400(X), where X includes at least one of: Al, Fe, In, or Sc (such as MFM-400(In) or MFM-400(Al)), MFM-520, UiO-66, UiO-67, ZIF-8, $Cu_3(HHTP)2$, $Ni(HTTP)_2$, $Cu_3(hexaiminobenzene)_2$, HKUST-1, $Cu[Ni[2,3-pyrzinedithiolate)_2]$, Cu-TCPP, as well as combinations of these with one another and/or with M-MOF-74.

Example ligands that may be utilized in a MOF may include and/or may be formed from one or more dicarboxylic acids, tricarboxylic acids, tetracarboxylic acids, or imidazolates, as well as combinations of these. Example dicarboxylic acids that may be utilized include 1,4-benzenedicarboxylic acid, enedioic acid, napthalene-1,4-dicarboxylic, 4-(4-carboxyphenyl)benzoic acid, thiophenedicarboxylic acid, [1,1'-biphenyl]-4,4'-dicarboxylic acid, or 5,5'-bis(carboxylateethenyul)-2,2'-bipyridine, as well as combinations of these. Example tricarboxylic acids that may be utilized include benzene-1,3,5-tricarboxylic acid, 4,4',4"-(S)-triazine-2,4,6-triyl-tribenzoic acid, or 4,4',4"benzene-1,3,5-triyl-tribenzoic acid, as well as combinations of these. Example tetracarboxylic acids that may be utilized include benzene-1,2,4,5-tetracarboxylic acid, meso-tetrakis(4-carboxylicphenyl) porphyrin acid, 3,3',5,5'-azobenzene tetracarboxylic acid, or 4,4',4''',4'''-(pyrene-1,3,6,8-tetrayl)tetrabenzoic acid, as well as combinations of these. Example imidazolates that may be utilized include 2-ethyl-1H-imidazole, 2-methyl-1H-imidazole, or 3-methyl-1H-benzimidazole, as well as combinations of these. Further ligands that may be utilized in a MOF may include and/or may be formed from: 1,4-Di(4'-pyrazolyl)benzene, 1,4,7,10-Tetraazacyclododecane-N,N',N'',N'''-tetraacetic acid, 2,4,6-(Tri-4-pyridinyl)-1,3,5-triazine, tris(isobutylaminoethyl) amine, 2,5-dihydroxyterephthalic acid, 2,6-naphthalenedicarboxylic acid, 1,4-phenylenediacetic acid, 1,1,2,2-tetra(4-carboxylphenyl)ethylene, 1,3,5-tricarboxybenzene, 1,3,5-tris(4-carboxyphenyl)benzene, or 2-(diphenylphosphino) terephthalic acid, as well as combinations of these. Additionally, or in the alternative, a MOF may include one or more paramagnetic lanthanides.

Example target gaseous substances that may be adsorbed, such as preferentially adsorbed, by a MOF may include one or more nitrogen oxides (NOx), one or more sulfur oxides (SOx), carbon monoxide (CO), carbon dioxide ($CO_2$), iodine ($I_2$), hydrogen sulfide ($H_2S$), ozone ($O_3$), or methane ($CH_4$), or water ($H_2O$), as well as combinations of these. NOx may include nitrogen dioxide ($NO_2$), nitric oxide (NO), nitrous oxide ($N_2O$), nitrate radical ($NO_3$), or dinitrogen pentoxide ($N_2O_5$), as well as combinations of these. SOx may include sulfur dioxide ($SO_2$), sulfur trioxide ($SO_3$), sulfur monoxide (SO), or disulfur monoxide ($S_2O$), as well as combinations of these. One or more electrical properties (e.g., resistance, capacitance, and/or inductance) of the MOF 204 may be augmented by and/or may depend at least in part on a presence and/or a concentration of one or more of these or other gaseous substances adsorbed by the MOF 204. One or more electrical parameters (e.g., voltage, amplitude, duration, polarity, frequency, and/or phase) of the discrimination pulses that propagate through the MOF 204 may be augmented by and/or may depend at least in part on the one or more electrical properties of the MOF 204, for example, as a result of the MOF 204 having been augmented the presence and/or the concentration of one or more of these or other gaseous substances adsorbed by the MOF.

Example MOFs may have an electrical resistance under a nominal condition, representing before exposure to a target gaseous substance, of from 0.1 gigaohm (GΩ) to 50 GΩ, such as from 0.1 GΩ to 1 GΩ, such as from 1 GΩ to 10 GΩ, such as from 15 GΩ to 30 GΩ, or such as from 35 GΩ to 50 GΩ. The electrical resistance of an MOF may decrease from the nominal condition, for example, proportionally, as a result of the target gaseous substance having been adsorbed by the MOF. The decrease in electrical resistance from the nominal condition may be on the order of from $1\times10^1$ to $1\times10^7$, such as from $1\times10^1$ to $1\times10^3$, such as from $1\times10^3$ to $1\times10^5$, or such as from $1\times10^5$ to $1\times10^7$.

Example MOFs may have a capacitance under a nominal condition, representing before exposure to a target gaseous substance, of from 10 picofarads (pF) to 10,000 pF, such as from 10 pF to 100 pF, such as from 20 pF to 80 pF, such as from 40 pF to 60 pF, such as from 100 pF to 500 pF, such as from 500 pF to 1,000 pF, or such as from such as from 1,000 pF to 10,000 pF. Example MOFs may have a specific capacitance, as determined at a current density of 1 ampere-per-gram of from 10 farad-per-gram (F/g) to 1,500 F/g, such as from 10 F/g to 50 F/g, such as from 50 F/g to 100 F/g, such as from 100 F/g to 200 F/g, such as from 200 F/g to 400 F/g, such as from 400 F/g to 800 F/g, such as from 800 F/g to 1,100 F/g or such as from 1,100 F/g to 1,500 F/g. The specific capacitance of an MOF may be determined at a scanning speed of 10 millivolts-per-second. The capacitance and/or specific capacitance of an MOF may increase, for example, proportionally, as a result of the target gaseous substance having been adsorbed by the MOF. The increase in capacitance and/or specific capacitance from the nominal condition may be on the order of from $1\times10^1$ to $1\times10^5$, such as from $1\times10^1$ to $1\times10^3$, such as from $1\times10^2$ to $1\times10^4$, or such as from $1\times10^3$ to $1\times10^5$.

Example gas detection apparatuses 100 may be configured to determine a presence and/or a concentration of a gaseous substance adsorbed by an MOFs from an environment containing less than 10 parts-per-million (ppm), such as from 0.1 ppm to 10 ppm, such as from 0.5 ppm to 5 ppm, or such as from 5 ppm to 10 ppm. Of course, higher concentrations of a gaseous substance may also be detected.

Referring further to FIG. 2, the sensor discriminator 200 may include a discrimination module 218 and a sensor simulator 220. The gas capture sensor 102 may be electrically coupled to the discrimination module 218 by the discriminator circuitry 104. The sensor simulator 220 may be electrically coupled to the power source 210 and the discrimination module 218 by simulation circuitry 222. The power source 210 may provide electrical pulses to the sensor simulator 220 via the simulation circuitry 222. The pulse module 212 may be configured to cause the power source 210 to provide the electrical pulses to the gas capture sensor 102, for example, periodically or intermittently according to a pulse interval or a pulse prompt. An electrical pulse that propagates through the sensor simulator 220 is sometimes referred to herein as a "simulation pulse" or a "simulation signal." Discrimination pulses that propagate through the MOF 204 may be provided to the discrimination module 218 via the discriminator circuitry 104. Simulation pulses that propagate through the sensor simulator 220 may be provided to the discrimination module 218 via the simulation circuitry 222.

The sensor simulator 220 may include at least one simulation component 224 configured to augment and/or otherwise cause the simulation pulses to simulate discrimination pulses propagating through the MOF 204 under at least one simulation condition. The at least one simulation component 224 may have one or more electrical properties (e.g., resistance, capacitance, and/or inductance) that correspond to (e.g., simulate) one or more electrical properties (e.g., resistance, capacitance, and/or inductance) of the MOF 204 under the at least one simulation condition. The simulation pulses may propagate through the at least one simulation component 224.

Example sensor simulator 220 and/or respective simulation components 224 may have an electrical resistance under a simulation condition, such as a simulation condition representing before exposure to a target gaseous substance, of from 0.001 gigaohm (GΩ) to 50 GΩ, such as from 0.001 GΩ to 0.1 GΩ, such as from 0.1 GΩ to 0.5 GΩ, such as from 0.1 GΩ to 1 GΩ, such as from 1 GΩ to 10 GΩ, such as from 15 GΩ to 30 GΩ, or such as from 35 GΩ to 50 GΩ. Additionally, or in the alternative, example sensor simulator 220 and/or respective simulation components 224 may have a capacitance under the condition of from 10 picofarads (pF) to 10,000 pF, such as from 10 pF to 100 pF, such as from 100 pF to 500 pF, such as from 500 pF to 1,000 pF, or such as from such as from 1,000 pF to 10,000 pF.

The simulation pulses may be provided periodically or intermittently, such as according to a pulse interval or a pulse prompt determined, for example, by the timer 214 or the computing device 300 (FIG. 1). At least one electrical parameter of the simulation pulses (e.g., voltage, amplitude, duration, polarity, frequency, and/or phase) may be augmented based at least in part on the one or more electrical properties of the at least one simulation component 224. The at least one electrical parameter of a simulation pulse (e.g., voltage, amplitude, duration, polarity, frequency, and/or phase) that passes through the simulation component 224 may correspond to (e.g., simulate) a corresponding electrical parameter (e.g., voltage, amplitude, duration, polarity, frequency, and/or phase) of a discrimination pulse that passes through the MOF 204 under the at least one simulation condition.

In some embodiments, the at least one simulation component 224 may include at least one resistor and/or at least one capacitor. By way of illustration, a resistance of the at least one simulation component may correspond to (e.g., simulate) a resistance of the MOF 204 under the at least one simulation condition. Additionally, or in the alternative, a capacitance of the at least one simulation component may correspond to (e.g., simulate) a capacitance of the MOF 204 under the at least one simulation condition. Additionally, or in the alternative, an inductance of the at least one simulation component may correspond to (e.g., simulate) an inductance of the MOF 204 under the at least one simulation condition.

In some embodiments, the sensor simulator 220 and/or the at least one simulation component 224 may include at least one integrated circuitry component, such as at least one processor and/or at least one memory device, configured to provide and/or augment simulation pulses that include at least one electrical parameter (e.g., voltage, amplitude, duration, polarity, frequency, and/or phase) that corresponds to (e.g., simulates) an electrical parameter (e.g., voltage, amplitude, duration, polarity, frequency, and/or phase) of a discrimination pulse that passes through the MOF 204 under the at least one simulation condition. The at least one integrated circuitry component may include at least one memory device that includes and/or defines the at least one simulation condition. The at least one simulation condition may be constant or variable. Additionally, or in the alternative, the at least one simulation condition may be determined based at least in part on a simulation algorithm, a simulation table, or the like. The at least one memory device may additionally or alternatively include computer-executable instructions, which when executed by the at least one processor, cause the at least one integrated circuitry component to provide and/or augment simulation pules that simulate discrimination pulses propagating through the MOF 204 under the at least one simulation condition. In some embodiments, sensor simulator 220 may cause the power source 210 to emit simulation pulses that propagate through the simulation circuitry. Additionally, or in the alternative, sensor simulator 220 may output a value from a computer-based simulation that represents a simulation pulse propagating through the sensor simulator 220 and/or the at least one simulation component 224. In at least one example, the computer-based simulation may include and/or utilize a lookup table. In at least one example, a simulation circuitry may include a memory device that stores one or more electrical properties corresponding to at least one simulation condition.

In some embodiments, the at least one simulation condition may correspond to (e.g., simulate) the MOF 204 under a nominal state. The nominal state may include and/or represent a state prior to exposing the MOF 204 to the at least one gaseous substance detectable or to be detected by the gas detection apparatus 100. Additionally, or in the alternative, the nominal state may include and/or represent a nominal exposure to the at least one gaseous substance detectable or to be detected by the gas detection apparatus 100. The nominal exposure may include and/or represent a baseline exposure to the at least one gaseous substance, such as a minimum acceptable exposure level. Additionally, or in the alternative, the nominal exposure may include and/or represent an exposure to a nominal gaseous environment, such as a gaseous environment that is devoid of the at least one gaseous substance. In some embodiments, a nominal gaseous environment, though devoid of the at least one gaseous substance, may augment and/or change to the one or more electrical properties of the MOF 204, such as over a period of time. The simulation of the nominal state may include and/or represent the augmentation and/or change imparted to the one or more electrical properties of the MOF 204 by exposure to the nominal gaseous environment.

Referring further to FIG. 2, the discrimination module 218 may receive the discrimination pulses from the gas capture sensor 102 and the simulation pulses from the sensor simulator 220. The discrimination module 218 may include a comparator 226 configured to compare a discrimination pulse to a simulation pulse. A comparison of the discrimination pulse to the simulation pulse may include a comparison of one or more electrical parameters of the discrimination pulses to one or more corresponding electrical parameters of the simulation pulse. In some embodiments the comparator 226 may determine a difference between a discrimination pulse and a simulation pulse, such as a difference between one or more respective electrical parameters of the discrimination pulse and the simulation pulse. The one or more electrical parameters compared by the comparator 226 may include voltage, amplitude, duration, polarity, frequency, and/or phase. For example, the comparator 226 may determine a voltage difference, an amplitude difference, a duration difference, a polarity difference, a frequency difference, and/or a phase difference, as between a discrimination pulse and a simulation pulse. The discriminator outputs 208 may include and/or may be based at least in part on the comparison of, such as the difference between, the discrimination pulses and the simulation pulses.

The discriminator outputs 208 may have an amplitude that depends at least in part on a magnitude of the discrimination pulse received by the discrimination module. Additionally, or in the alternative, the discriminator outputs 208 may have an amplitude that depends at least in part on the comparison of the discrimination pulse to the simulating pulse. For example, the discriminator outputs 208 may have an amplitude that depends at least in part on the magnitude of the difference between the discrimination pulse and the simulation pulse. By way of example, the discriminator outputs 208 may include a voltage that depends at least in part on a difference between a voltage of the discrimination pulse and a voltage of the reference value. As another example, the discriminator outputs 208 may have a polarity that depends at least in part on the sign of the difference (e.g., positive or negative) between the discrimination pulse and the simulation pulse.

In some embodiments, the discrimination module 218 may include an amplifier 228. The amplifier 228 may amplify the discriminator outputs 208. Additionally, or in the alternative, the amplifier 228 may amplify the discrimination pulses and/or the simulation pulses, such as prior to being compared to one another. In some embodiments, the amplifier 228 may include or may be configured as a pulse shaping amplifier.

In some embodiments, the discrimination module 218 may include or may be configured as an integral discriminator. The integral discriminator may provide a discriminator output 208 when, such as only when, the difference between a discrimination pulse and a reference value, such as a simulation pulse, exceed a threshold. Additionally, or in the alternative, the discrimination module 218 may include or may be configured as a differential discriminator. The differential discriminator may provide a discriminator output 208 when, such as only when, the difference between a discrimination pulse and a reference value, such as a simulation pulse, is between a lower discriminator level and an upper discriminator level.

In some embodiments, the discrimination module 218 may include a counter 230. The counter 230 may be configured to accumulate a number of discrimination outputs that correspond to a specified value or range. The specified value include a threshold difference between the discrimination pulse and the simulation pulse exceeds. The specified range may include a range between a lower value and an upper value. The discriminator outputs 208 may include and/or may represent a count-based and/or a time-based output of the number of discrimination pulses that correspond to the specified value or range. The count-based output may represent the number of discrimination outputs accumulated over a specified time interval. The time-based output may represent a time interval corresponding a specified number of accumulated discrimination outputs. Additionally, or in the alternative, the computing device 300 (FIG. 1) may include a counter 230 configured to accumulate the number of discriminator outputs 208 that correspond to a specified value or range. Additionally, or in the alternative, the discrimination module 218 and/or the computing device 300 (FIG. 1) may be configured to perform a Laplace transform and/or a Fourier transform upon the discrimination pulses received by the discrimination module and/or the discriminator outputs 208.

In some embodiments, the discrimination module 218 may include a digital pulse processing system. The digital pulse processing system may digitize the discrimination pulses received by the discrimination module and/or the discriminator outputs 208, for example, using a digital processor, such as a field programmable gate array or a digital signal processor.

In some embodiments, the sensor discriminator 200 may include feedback circuitry 232 electrically coupling the discrimination module 218 to the sensor simulator 220. The feedback circuitry 232 may provide a feedback output from the discrimination module 218 to the sensor simulator 220. In some embodiments, the feedback output may include and/or may be based at least in part on a discriminator output 208. The sensor simulator 220 may utilize a feedback output to determine and/or augment a simulation pulse provided to the discrimination module 218.

Additionally, or in the alternative, in some embodiments, the sensor discriminator 200 may include feedforward circuitry 234 electrically coupling the discrimination module 218 to the discriminator circuitry 104. The feedforward circuitry 234 may provide a feedforward input to the sensor simulator 220 from the gas capture sensor 102. In some embodiments, the feedforward input may include and/or may be based at least in part on a discrimination pulse. The sensor simulator 220 may utilize a feedforward input to determine and/or augment a simulation pulse provided to the discrimination module 218.

Referring now to FIG. 3, exemplary gas detection systems 400 are further described. A gas detection system 400 includes at least one computing device 300. As shown, a computing device 300 may include at least one processor 306 and at least one memory device 308. The at least one processor 306 may include a microprocessor, microcontroller, integrated circuitry, logic device, and/or other suitable processing device. The at least one memory device 308 may include a computer-readable media or medium, such as a non-transitory computer-readable media or medium.

As used herein, the terms "computer-readable media" and "non-transitory computer-readable media" refer to any and all forms of computer-readable media or medium except for a transitory, propagating signal. The computer-readable media may include volatile and/or nonvolatile media, removable and/or nonremovable media, media readable by a database, as well as combinations of these. For example, computer-readable media may include (but is not limited to): RAM, ROM, EEPROM, flash memory or other memory technology, CD-ROM, digital versatile discs (DVD), holographic media or other optical disc storage, magnetic cassettes, magnetic tape, magnetic disk storage, or other magnetic storage devices, as well as combinations of these. Computer-readable media may store data temporarily or permanently. However, unless explicitly specified otherwise, the term "computer-readable media" should not be construed to include physical, but transitory, forms of propagating signal transmissions, such as: radio waves in a transitory, propagating state, electrical signals in a transitory, propagating state, or light pulses in a transitory, propagating state.

The at least one memory device 308 may store information accessible by the at least one processor 306, such as instructions, data structures, program modules, and other data representations. The at least one memory device 308 may include computer-executable instructions 310 that can be executed by the at least one processor 306. The instructions 310, when executed by the at least one processor 306 may cause the at least one processor 306 to perform operations, including operations associated with the gas detection system 400 and/or at least one gas detection apparatus 100. The operations may include operations associated with a sensor discriminator 200, such as operations associated with one or more elements of a sensor discriminator 200, such as a discrimination module 218, a power source 210, a timer 214, and/or a sensor simulator 220. The operations may include causing a sensor discriminator 200 to generate a discriminator output 208. Additionally, or in the alternative, the operations may include generating, determining, transmitting, and/or receiving a discriminator output 208, and/or determining, transmitting, and/or receiving one or more electrical properties, such as resistance, capacitance, or impedance, of a MOF 204 based at least in part on the discriminator output 208. Additionally, or in the alternative, the operations may include operations associated with the monitoring system 302 and/or the control system 304.

The at least one memory device 308 may store data 312 accessible by the at least one processor 306. The data 312 may include instructions, data structures, program modules, and other data representations. The data 312 may include current or real-time data, past data, or a combination thereof. The data 312 may be stored in a data library 314. As examples, the data 312 may include data associated with or generated by the gas detection system 400 and/or at least one gas detection apparatus 100, such as data 312 associated with generating, determining, transmitting, and/or receiving discriminator outputs 208, and/or data 312 associated with determination of a presence and/or a concentration of at least one gaseous substance, and/or data 312 associated with the monitoring system 302 and/or the control system 304. The data 312 may also include other data sets, parameters, outputs, information, associated with the gas detection system 400 and/or operations thereof.

The gas detection system 400 may include one or more system modules 316 stored in the at least one memory device 308. The one or more modules may include and/or may be referenced by computer-executable instructions 310 that can be executed by the at least one processor 306. The one or more system modules 316 may include at least one discrimination module 218 (FIG. 2). Additionally, or in the alternative, the one or more system modules 316 may include at least one monitoring module associated with the monitoring system 302. The monitoring system 302 may include at least one user interface 318, and at least one monitoring module may be configured to cause the at least one processor 306 to provide monitoring commands to the at least one user interface 318, such as monitoring commands based at least in part on discriminator outputs 208. By way of example, the user interface 318 may include a visual display device, such as a monitor, a light, or the like. The user interface 318 may be operable to generate a visual representation based at least in part on the monitoring commands. Additionally, or in the alternative, the user interface may include an audible device, such as a speaker, a siren, or the like. The user interface 318 may be operable to generate an audible representation based at least in part on the monitoring commands. Additionally, or in the alternative, the user interface 318 may include one or more user input devices configured to allow a user to interact with the gas detection system 400 and/or at least one computing device 300. The monitoring commands may be configured to cause the at least one user interface 318 to generate a visual and/or audible representation indicative of the presence and/or the concentration of the at least one gaseous substance. The visual and/or audible representation may include qualitative and/or quantitative information corresponding to the at least one gaseous substance, such as a presence and/or a concentration of the at least one gaseous substance. Additionally, or in the alternative, such as visual and/or audible warnings, alarms, or status levels.

Additionally, or in the alternative, the one or more system modules 316 may include at least one control module associated with the control system 304. The control system 304 may include at least one controllable component 320, and at least one control module may be configured to cause the at least one processor 306 to provide control commands to the at least one controllable component 320, such as control commands based at least in part on discriminator outputs 208, and/or such as responsive a determination of a presence and/or a concentration of at least one gaseous substance. Additionally, or in the alternative, the control commands may be responsive to data generated and/or stored based least in part on the discriminator outputs. In some embodiments, at least one controllable component may be configured to control at least one process parameter associated with the gas detection system 400, such as at least one process parameter of a system or apparatus associated with a formation, presence, remediation, and/or concentration of the at least one gaseous substance. For example, the at least one controllable component may control the formation, presence, remediation, and/or concentration of the at least one gaseous substance based at least in part on the control commands.

Still referring to FIG. 3, the computing device 300 may include a communication interface 322. The communication interface 322 may communicatively couple the computing device 300 with at least one gas-sensor 108. Additionally, or in the alternative, the communication interface 322 may communicatively couple the computing device 300 with the monitoring system 302 and/or the control system 304. The communication interface 322 may be configured for communications with a communication network 324 via wired or wireless communication links 326. The communication interface 322 may include any suitable components for interfacing with one or more network(s), including for example, transmitters, receivers, ports, controllers, antennas, and/or other suitable components. The communication interface 322 may allow the at least one computing device 300 to communicate with various nodes on the communication network 324. The communication network 324 may include, for example, a local area network (LAN), a wide area network (WAN), SATCOM network, VHF network, a HF network, a Wi-Fi network, a WiMAX network, a gatelink network, and/or any other suitable communication network 324 for transmitting messages to and/or from the at least one computing device 300 across the communication links 326. The communication links 326 of communication network 324 may include a combination of wired and/or wireless communication links.

The communication interface 322 may additionally or alternatively allow the at least one computing device 300 to communicate with a management system 328. The management system 328 may be configured to interact with the at least one computing device 300 in connection with enterprise-level operations pertaining to the gas detection system 400. Such enterprise level operations may include transmitting data from the management system 328 to the at least one computing device 300 and/or transmitting data from the at least one computing device 300 to the management system 328. The management system 328 may include a server 330 and/or a data warehouse 332. As an example, at least a portion of the data 312 may be stored in the data warehouse 332. The server 330 may be configured to transmit data 312 from the data warehouse 332 to the at least one computing device 300, and/or to receive data 312 from the at least one computing device 300 and to store the received data 312 in the data warehouse 332 for further purposes. The server 330 and/or the data warehouse 332 may be implemented as part of a computing device 300 and/or as part of the management system 328. The management system 328, the server 330, and/or the data warehouse 332 may include at least one computing device 300 configured, for example, as described with reference to FIG. 3.

Referring now to FIGS. 4A-4E, example gas detection systems 400 are further described. The presently disclosed subject matter may be useful in a variety of contexts and/or implementations, as exemplified by the gas detection systems 400 described with reference to FIGS. 4A-4E. The examples described with reference to FIGS. 4A-4E are not intended to limit the present disclosure, and other useful contexts and/or implementations of the presently disclosed subject matter will be appreciated, including upon considering the example gas detection systems 400 are described with reference to FIGS. 4A-4E.

As shown in FIG. 4A, a gas detection system 400 may be implemented in association with a combustion system 402 configured to perform a combustion process that includes combusting a combustion source 404 to perform work 406. The combustion source 404 may include at least one fuel, at least one oxidizer, and at least one heat source. The work 406 may include a transfer of energy to or from an object by imparting a force along a displacement. The work 406 may generate and/or store power, such as mechanical power, electrical power, and/or chemical power. The combustion process performed by the combustion system 402 may generate combustion products 408. The combustion system 402 may include at least one gas-sensor 108, such as at least one smart gas-sensor 110, configured to determine a presence and/or a concentration of one or more gaseous substances. For example, the at least one gas-sensor 108 may determine a presence and/or a concentration of one or more gaseous substances in the combustion products 408 generated by the combustion system 402. The combustion system 402 may include at least one controllable component 320 configured to control at least one operation of the combustion system 402 and/or at least part of the combustion process performed by the combustion system 402. An operation of the combustion system 402 and/or combustion process may be controlled by a controllable component 320 based at least in part on the presence and/or the concentration of the one or more gaseous substances determined by the at least one gas-sensor 108. By way of example, the combustion system 402 may include a combustion engine, such as a combustion engine associated with a vehicle, such as an automobile, an aircraft, or a marine vessel. As another example, the combustion system 402 may include and/or may define a portion of a fossil fuel power station. The combustion system 402 may be configured to generate thermal energy from chemical energy stored in fossil fuels. The fossil fuel power station may convert the thermal energy generated by the combustion system 402 into mechanical energy and may convert the mechanical energy into electrical energy.

As shown in FIG. 4B, a gas detection system 400 may be implemented in association with at least one point source 410. A point source 410 may define a single identifiable localized source of at least one gaseous substance. The point source 410 may be associated with a process system 412. The process system 412 may include and/or generate at least one process stream 414. A process stream 414 may include, and/or may transition into, a discharge stream 416. The point source 410 may be located at the discharge stream 416, such as at a transition from the process stream 414 to the discharge stream 416. The discharge stream 416 may include a discharge of the process stream 414 into air or water. The gas detection system 400 may include at least one gas-sensor 108, such as at least one smart gas-sensor 110, configured to determine a presence and/or a concentration of at least one gaseous substance at the point source 410. For example, the at least one gas-sensor 108 may determine a presence and/or a concentration of one or more gaseous substances generated by the process system 412 and/or otherwise in the process stream 414 or discharge stream 416. The gas detection system 400 may include at least one controllable component 320 configured to perform control operations with respect to the process system 412. The at least one controllable component 320 may perform the control operations responsive to control commands from a computing device 300, for example, based at least in part on the presence and/or the concentration of the one or more gaseous substances at the point source 410 determined by the at least one gas-sensor 108. In some embodiments, the gas detection system 400 may decrease a presence and/or a concentration of the one or more gaseous substances generated by the process system 412 at least in part by providing control commands to the at least one controllable component 320 to control the least one operation of the process system 412. By way of example, the process system 412 may include an industrial processing plant, such as a manufacturing facility, a power generation facility, a refinery, or the like. The point source 410 may include or define a wastewater discharge outlet, or an airborne discharge outlet. In some embodiments, the point source 410 may include a flue-gas stack, a smokestack, a chimney, or the like. In some embodiments, the point source 410 may be associated with a combustion system 402. For example, the process system 412 may include a combustion system 402, and/or the combustion system may produce a discharge stream 416 at the point source 410.

As shown in FIG. 4C, a gas detection system 400 may be implemented in association with an area source 420. An area source 420 may define a geographic area that may be a source of at least one gaseous substance. The gas detection system 400 may include at least one gas-sensor 108, such as at least one smart gas-sensor 110, configured to determine a presence and/or a concentration of at least one gaseous substance at, around, or within the area source 420. In some embodiments, the gas detection system 400 may include a plurality of gas-sensors 108 distributed about one or more area sources 420. One or more of the gas-sensors 108 may be associated with coordinates 422 that identify a location of the respective gas-sensor 108, such as a location within a corresponding area source 420. The coordinates of a gas-sensor 108 may include geographic coordinates, global positioning system coordinates, or the like. One or more of the gas-sensors 108 may be continuously or intermittently communicatively coupled to a monitoring system 302. A gas-sensor 108 may include a communication interface 322 configured to communicate with a monitoring system 302, continuously or intermittently, via wired or wireless communication links 326. The communication interface 322 of a gas-sensor 108 may include a wireless communication device 424 that utilizes a suitable wireless communication technology. The wireless communication device 424 may include an RFID device (e.g., a PRAT RFID device, a ARPT RFID device, or an ARAT RFID device), a Zigbee device, a Bluetooth device, an IrDA device, a cellular device (e.g., a GSM device, a PCS device, a D-AMPS device, an LTE device, a 5G device, a 4G device, a 3G device), or the like.

Communications with the monitoring system 302 may include transmitting discriminator outputs 208 from the gas-sensor 108 to the monitoring system 302. In some embodiments, a gas-sensor 108 located at, around, or within an area source 420 may be a smart gas-sensor 110 that includes a computing device 300 configured to cause the wireless communication device 424 to transmit discriminator outputs 208 and/or data 312 to the monitoring system 302. Additionally, or in the alternative, the monitoring system 302 may be configured to interrogate a gas-sensor 108 located at, around, or within an area source 420 to obtain discriminator outputs 208 and/or data 312 from the gas-sensor 108. The monitoring system 302 may include and/or may be communicatively coupled with at least one computing device 300 configured to receive and/or process the discriminator outputs 208 from one or more of the gas-sensors 108, such as from the plurality of gas-sensors 108 distributed about the one or more area sources 420. Additionally, or in the alternative, the monitoring system 302 may include and/or may be communicatively coupled with a management system 328 configured to perform enterprise-level operations pertaining to the gas detection system 400.

The monitoring system 302 and/or the one or more gas-sensors 108 may be configured to determine a presence and/or a concentration of at least one gaseous substance at, around, or within the area source 420. The monitoring system 302 may be configured to report data 312 pertaining to the presence and/or the concentration of the at least one gaseous substance determined from one or more gas-sensors 108 located at, around, or within the area source 420. By way of example, an area source 420 may include at least a portion of one or more of the following: an industrial plant, a manufacturing facility, a chemical manufacturing facility, a foundry, a farm, an agricultural facility, a hazardous waste processing or incineration facility, a waste treatment facility, a mining site, a landfill, a hydrocarbon production facility, a municipality, a land tract, a body of water, a building, a volatile liquid spill, a forest fire, or a pollution remediation site. In some embodiments, an area source 420 may include one or more point sources 410.

As shown in FIG. 4D, a gas detection system 400 may be implemented in association with at least one mobile device 430 that includes at least one gas-sensor 108, such as a smart gas-sensor 110. As shown, in some embodiments, the at least one mobile device 430 may include a wearable device 432. Additionally, or in the alternative, the at least one mobile device 430 may include a cellular device 434, such as a mobile phone, a tablet, a smart watch, a head-mounted device, or the like. As shown, a wearable device 432 may include an attachment element 436, such as a strap, a band, a sleeve, a lanyard, or the like. The attachment element 436 may be configured to attach to a body part of a user and/or to an article of clothing worn by the user. For example, as shown, the wearable device 432 may be attached to a user's arm or wrist. A mobile device 430 may be configured to determine a presence and/or a concentration of at least one gaseous substances at a user's location. Additionally, or in the alternative, the mobile device 430 may be configured to determine and/or track a user's exposure to at least one gaseous substance, and/or to identify a location associated with the user's exposure to the at least one gaseous substance.

In some embodiments, the mobile device 430 may include a location tracking system 438, such as a geographic coordinate tracking system, a global positioning tracking system, or the like. The location tracking system 438 may track a location of the mobile device 430. The location of the mobile device 430 may be associated with discriminator outputs 208 from the at least one gas-sensor 108 and/or data 312 associated therewith. A presence and/or a concentration of at least one gaseous substance may be determined for at least one location of the mobile device 430, for example, based at least in part on the discriminator outputs 208 from the at least one gas-sensor 108 and the location of the mobile device 430 determined by the location tracking system 438. In some embodiments, the mobile device 430 may include a communication interface 322, such as a wireless communication device 424 (e.g., an RFID device, a Zigbee device, a Bluetooth device, an IrDA device, a cellular device, or the like). The communication interface 322 of the mobile device 430 may be configured to communicate with a monitoring system 302, continuously or intermittently, via a wired or wireless communication link 326. Additionally, or in the alternative, the mobile device 430 may communicate with a monitoring system 302 via a docking station (not shown). In some embodiments, a mobile device 430 may include a computing device 300 configured to perform operations associated with the at least one gas-sensor 108, the location tracking system 438, and/or the wireless communication device 424.

Communications between the mobile device 430 and the monitoring system 302 may include transmitting discriminator outputs 208 from the mobile device 430 to the monitoring system 302. In some embodiments, the mobile device 430 may include a computing device 300 configured to cause the wireless communication device 424 to transmit discriminator outputs 208, and/or location data 312 to the monitoring system 302. Additionally, or in the alternative, the monitoring system 302 may be configured to interrogate the wireless communication device 424 to obtain discriminator outputs 208 and/or location data 312. The monitoring system 302 may include and/or may be communicatively coupled with at least one computing device 300 configured to receive and/or process the discriminator outputs 208 and/or location data 312 from one or more mobile devices 430. Additionally, or in the alternative, the monitoring system 302 may include and/or may be communicatively coupled with a management system 328 configured to perform enterprise-level operations pertaining to the gas detection system 400.

In some embodiments, the mobile device 430 may include a user interface 318. In some embodiments, the user interface 318 may be configured to provide a visual and/or audible representation corresponding to the user's exposure to the at least one gaseous substance, such as a visual and/or audible warning, alarm, or status level a with respect to the presence and/or the concentration of the at least one gaseous substance. In some embodiments, the mobile device 430 may track a user's exposure to the at least one gaseous substance in association with a location of the user at, around, or within an area source 420 and/or point source 410, for example, in association with work or personal activities.

As shown in FIG. 4E, a gas detection system 400 may be implemented in association with a vehicle 440, such as an automobile, an aircraft, or a marine vessel. As shown, the vehicle 440 may be an autonomous vehicle 442. The autonomous vehicle 442 may be an autonomous automobile, an autonomous aircraft, or an autonomous marine vessel. The autonomous vehicle 442 may be unmanned. Additionally, or in the alternative, a vehicle 440, such as an autonomous vehicle 442 may be configured to transport one or more persons, such as operators and/or passengers. In some embodiments, the vehicle 440 may include one or more propellers 444 configured to cause the vehicle to fly. The vehicle 440 may include at least one gas-sensor 108 configured to determine a presence and/or a concentration of at least one gaseous substances, such as at a location of the vehicle 440.

In some embodiments, the vehicle 440 may include a location tracking system 438, such as a geographic coordinate tracking system, a global positioning tracking system, or the like. The location tracking system 438 may track a location of the vehicle 440. The location of the vehicle 440 may be associated with discrimination outputs 208 from the at least one gas-sensor 108 and/or data 312 associated therewith. A presence and/or a concentration of at least one gaseous substance may be determined for at least one location of the vehicle 440, for example, based at least in part on the discriminator outputs 208 from the at least one gas-sensor 108 and the location of the vehicle 440 determined by the location tracking system 438. In some embodiments, the vehicle 440 may include a communication interface 322, such as a wireless communication device 424 (e.g., an RFID device, a Zigbee device, a Bluetooth device, an IrDA device, a cellular device, or the like). The communication interface 322 of the vehicle 440 may be configured to communicate with a monitoring system 302, continuously or intermittently, via a wired or wireless communication link 326. Additionally, or in the alternative, the vehicle 440 may communicate with a monitoring system 302 via a docking station (not shown). In some embodiments, a vehicle 440 may include a computing device 300 configured to perform operations associated with the at least one gas-sensor 108, the location tracking system 438, and/or the wireless communication device 424.

Communications between the vehicle 440 and the monitoring system 302 may include transmitting discriminator outputs 208 from the vehicle 440 to the monitoring system 302. In some embodiments, the vehicle 440 may include a computing device 300 configured to cause the wireless communication device 424 to transmit discriminator outputs 208, and/or location data 312 to the monitoring system 302. Additionally, or in the alternative, the monitoring system 302 may be configured to interrogate the wireless communication device 424 to obtain discriminator outputs 208 and/or location data 312. The monitoring system 302 may include and/or may be communicatively coupled with at least one computing device 300 configured to receive and/or process the discriminator outputs 208 and/or location data 312 from one or more vehicles 440. Additionally, or in the alternative, the monitoring system 302 may include and/or may be communicatively coupled with a management system 328 configured to perform enterprise-level operations pertaining to the gas detection system 400. In some embodiments, the monitoring system 302 may track an exposure of one or more gas-sensors 108 on the vehicle 440 with respect to a location of the vehicle 440 at, around, or within an area source 420 and/or point source 410.

Referring now to FIG. 5, example methods associated with the presently disclosed gas detection apparatus 100 and/or gas detection systems 400 are further described. In some embodiments, an example method 500 may include detecting and/or monitoring a gaseous substance, such as detecting and/or monitoring a presence and/or a concentration of the gaseous substance. Additionally, or in the alternative, an example method 500 may include controlling a gaseous substance, such as controlling a presence and/or a concentration of the gaseous substance, for example, using one or more controllable components. Additionally, or in the alternative, an example method 500 may include operating a gas detection apparatus 100 and/or gas detection systems 400, and/or performing one or more operations associated therewith.

As shown, an example method 500 may include, at block 502, determining a discrimination pulse. The discrimination pulse may include a first electrical pulse from a power source 210 after having passed through a gas capture sensor 102 that includes a MOF 204. The MOF 204 may include at least one electrical property that depends at least in part on a presence and/or a concentration of the gaseous substance. The MOF 204 may augment the discrimination pulse based at least in part on the at least one electrical property.

At block 504, the method 500 may include determining a simulation pulse. The simulation pulse may include a second electrical pulse from the power source 210 after having passed through a sensor simulator 220 that includes at least one simulation component 224 configured to simulate the MOF 204 under at least one simulation condition. At block 506, the method 500 may include causing a discriminator output 208 that includes a comparison of the discrimination pulse and the simulation pulse in respect of at least one electrical property. The discriminator output may be indicative of the presence and/or the concentration of the gaseous substance.

In some embodiments, an example method 500 may include, at block 508, causing at least one discrimination pulse. The at least one discrimination pulse may be output by the power source 210. Additionally, or in the alternative, the method 500 may include, at block 510, causing at least one simulation pulse. The at least one simulation pulse may be output by the power source 210.

In some embodiments, an example method 500 may include, at block 512, causing at least one monitoring command. The at least one monitoring command may be provided to a monitoring system 302. For example, the monitoring system 302 may include a user interface 318, and the at least one monitoring command may be configured to control and/or operate the user interface 318. Additionally, or in the alternative, the method 500 may include, at block 514, causing the user interface 318 to output a visual and/or audible representation, for example, based at least in part on the at least one monitoring command.

In some embodiments, an example method 500 may include, at block 516, causing at least one control command. The at least one control command may be provided to a control system 304. For example, the control system 304 may include at least one controllable component 320, and the control system 304 may be configured to control and/or operate the at least one controllable component 320. Additionally, or in the alternative, the method 500 may include, at block 518, causing the at least one controllable component 320 to perform a control operation, for example, based at least in part on the at least one control command.

Further aspects of the present disclosure are provided by the following clauses:

A sensor discriminator for detecting at least one gaseous substance based on a change in at least on electrical property of a gas capture sensor, the sensor discriminator comprising: a power source; a discrimination module; a sensor simulator comprising at least one simulation component configured to simulate a metal organic framework under at least one simulation condition; a simulation circuitry electrically coupling the sensor simulator to the power source and the discrimination module; and a discriminator circuitry configured to electrically couple the power source and the discrimination module to the metal organic framework; wherein the discrimination module comprises a comparator configured to perform a comparison of a discrimination pulse to a simulation pulse in respect of at least one electrical property, the discrimination pulse comprising a first electrical pulse from the power source having passed through the metal organic framework, and the simulation pulse comprising a second electrical pulse from the power source having passed through the at least one simulation component of the sensor simulator; and wherein the discrimination module is configured to cause a discriminator output comprising the comparison of the discrimination pulse to the simulation pulse, wherein the at least one electrical property depends at least in part on at least one electrical parameter of the metal organic framework, the at least one electrical parameter of the metal organic framework augmented by a presence and/or a concentration of the at least one gaseous substance, and the discriminator output indicative of the presence and/or the concentration of the at least one gaseous substance.

The sensor discriminator of any clause herein, comprising: the metal organic framework electrically coupled to the discriminator circuitry.

The sensor discriminator of any clause herein, comprising: a timer electrically coupled to the power source, the timer configured to determine a pulse interval for at least one of the discrimination pulse and the simulation pulse.

The sensor discriminator of any clause herein, wherein the at least one simulation component comprises at least one of: at least one resistor, at least one capacitor, or at least one integrated circuit.

The sensor discriminator of any clause herein, wherein the discrimination module comprises at least one amplifier, the at least one amplifier configured to amplify at least one of: the discrimination pulse, the simulation pulse, or the discriminator output.

The sensor discriminator of any clause herein, wherein the discrimination module comprises at least one counter, the at least one counter configured to accumulate a number of discrimination outputs that correspond to at least one of a specified value or a specified range.

The sensor discriminator of any clause herein, wherein the at least one electrical property comprises a voltage.

The sensor discriminator of any clause herein, wherein the at least one gaseous substance comprises at least one of: one or more nitrogen oxides, one or more sulfur oxides, carbon monoxide, carbon dioxide, iodine, hydrogen sulfide, ozone, methane, or water.

The sensor discriminator of any clause herein, wherein the metal organic framework comprises at least one of the following divalent metallic cations: Zn, Mg, Mn, Co, Ni, Cu, Cd, or Fe.

The sensor discriminator of any clause herein, wherein the power source is configured to provide direct current electrical pulses, the direct current electrical pulses comprising an electrical potential of from 0.1 volt to 10 volts.

The sensor discriminator of any clause herein, wherein the power source is configured to provide direct current electrical pulses, the direct current electrical pulses comprising a pulse interval of from 1 micro-Hertz to 25 Hertz.

The sensor discriminator of any clause herein, comprising: a computing device, wherein the computing device comprises at least one processor and at least one memory device, the at least one memory device comprising a non-transitory computer-readable medium comprising computer-executable instructions, which, when executed by the at least one processor, cause the sensor discriminator to perform operations, the operations comprising: determining the discrimination pulse; determining the simulation pulse; and causing the discriminator output comprising the comparison of the discrimination pulse to the simulation pulse.

A sensor discriminator, comprising: a sensor simulator comprising at least one simulation component configured to simulate a metal organic framework under at least one simulation condition; a simulation circuitry electrically coupled to the sensor simulator; a discriminator circuitry electrically coupled the metal organic framework; and a comparator configured to perform a comparison of a discrimination pulse to a simulation pulse in respect of at least one electrical property, the discrimination pulse comprising a first electrical pulse having passed through the metal organic framework, and the simulation pulse comprising a second electrical pulse having passed through the at least one simulation component of the sensor simulator; wherein the comparator is configured to cause a discriminator output comprising the comparison of the discrimination pulse to the simulation pulse, wherein the at least one electrical property depends at least in part on at least one electrical parameter of the metal organic framework.

A sensor discriminator, comprising: a power source, a discrimination module, a sensor simulator comprising at least one simulation component configured to simulate a metal organic framework under at least one simulation condition; a simulation circuitry electrically coupling the sensor simulator to the power source and the discrimination module; and a discriminator circuitry electrically coupling the power source and the discrimination module to the gas capture probe.

The sensor discriminator of any clause herein, wherein the discrimination module comprises a comparator configured to perform a comparison of a discrimination pulse to a simulation pulse in respect of at least one electrical property, the discrimination pulse comprising a first electrical pulse from the power source having passed through the metal organic framework of the gas capture probe, and the simulation pulse comprising a second electrical pulse from the power source having passed through the at least one simulation component of the sensor simulator.

The sensor discriminator of any clause herein, wherein the discriminator output comprises the comparison of the discrimination pulse to the simulation pulse, wherein the at least one electrical property depends at least in part on at least one electrical parameter of the metal organic framework, and wherein the presence and/or the concentration of the at least one gaseous substance augments the at least one electrical parameter of the metal organic framework.

A gas-sensor, comprising: a gas capture sensor comprising a metal organic framework, and the sensor discriminator of any clause herein.

The gas-sensor of any clause herein, comprising: a sensor discriminator configured to provide a discriminator output indicative of a presence and/or a concentration of at least one gaseous substance adsorbed by the metal organic framework; the metal organic framework comprising a metal organic framework or an aluminosilicate material; and the sensor discriminator comprising: a power source; a discrimination module; a sensor simulator comprising at least one simulation component configured to simulate the metal organic framework under at least one simulation condition; a simulation circuitry electrically coupling the sensor simulator to the power source and the discrimination module; and a discriminator circuitry electrically coupling the power source and the discrimination module to the gas capture probe; wherein the discrimination module comprises a comparator configured to perform a comparison of a discrimination pulse to a simulation pulse in respect of at least one electrical property, the discrimination pulse comprising a first electrical pulse from the power source having passed through the metal organic framework of the gas capture probe, and the simulation pulse comprising a second electrical pulse from the power source having passed through the at least one simulation component of the sensor simulator; and wherein the discriminator output comprises the comparison of the discrimination pulse to the simulation pulse, wherein the at least one electrical property depends at least in part on at least one electrical parameter of the metal organic framework, and wherein the presence and/or the concentration of the at least one gaseous substance augments the at least one electrical parameter of the metal organic framework.

A gas detection system, comprising: at least one gas-sensor, the at least one gas-sensor comprising: a gas capture sensor comprising a metal organic framework, and a sensor discriminator configured to provide a discriminator output indicative of a presence and/or a concentration of at least one gaseous substance adsorbed by the metal organic framework; the metal organic framework comprising a metal organic framework or an aluminosilicate material; and the sensor discriminator comprising: a power source; a discrimination module; a sensor simulator comprising at least one simulation component configured to simulate the metal organic framework under at least one simulation condition; a simulation circuitry electrically coupling the sensor simulator to the power source and the discrimination module; and a discriminator circuitry electrically coupling the power source and the discrimination module to the gas capture probe; wherein the discrimination module comprises a comparator configured to perform a comparison of a discrimination pulse to a simulation pulse in respect of at least one electrical property, the discrimination pulse comprising a first electrical pulse from the power source having passed through the metal organic framework of the gas capture probe, and the simulation pulse comprising a second electrical pulse from the power source having passed through the at least one simulation component of the sensor simulator; and wherein the discriminator output comprises the comparison of the discrimination pulse to the simulation pulse, wherein the at least one electrical property depends at least in part on at least one electrical parameter of the metal organic framework, and wherein the presence and/or the concentration of the at least one gaseous substance augments the at least one electrical parameter of the metal organic framework.

The gas detection system of any clause herein, comprising: at least one controllable component, wherein the at least one gas-sensor is configured to determine the presences and/or concentration of the at least one gaseous substance in combustion products of a combustion system, and wherein the at least one controllable component is configured to control, based at least in part on the presence and/or concentration of the at least one gaseous substance, at least one operation of the combustion system and/or at least part of a combustion process performed by the combustion system.

The gas detection system of any clause herein, comprising at least one controllable component, wherein the at least one gas-sensor is configured to determine the presences and/or concentration of the at least one gaseous substance at a point source associated with a process system, and wherein the at least one controllable component is configured to perform a control operation with respect to the process system based at least in part on the presence and/or concentration of the at least one gaseous substance.

The gas detection system of any clause herein, wherein the at least one gas-sensor is configured to determine the presences and/or concentration of the at least one gaseous substance at an area source.

The gas detection system of any clause herein, comprising: a least one vehicle, wherein a respective one of the at least one vehicle comprises: a respective one of the at least one gas-sensor, and a location tracking system configured to track a location of the respective one of the at least one vehicle; and wherein the gas detection system is configured to determine the presences and/or concentration of the at least one gaseous substance at the location of the respective one of the at least one vehicle.

The gas detection system of any clause herein, comprising: a least one mobile device, wherein a respective one of the at least one mobile device comprises: a respective one of the at least one gas-sensor, and a location tracking system configured to track a location of the respective one of the at least one mobile device; and wherein the gas detection system is configured to determine the presences and/or concentration of the at least one gaseous substance at the location of the respective one of the at least one mobile device.

A method of monitoring a gaseous substance, the method comprising: determining a discrimination pulse, the discrimination pulse comprising a first electrical pulse from a power source having passed through a gas capture sensor comprising a metal organic framework, the metal organic framework comprising at least one electrical property dependent at least in part on a presence and/or a concentration of the gaseous substance, the metal organic framework augmenting the discrimination pulse based at least in part on the at least one electrical property; determining a simulation pulse, the simulation pulse comprising a second electrical pulse from the power source having passed through a sensor simulator comprising at least one simulation component configured to simulate the metal organic framework under at least one simulation condition; and causing a discriminator output comprising a comparison of the discrimination pulse and the simulation pulse in respect of the at least one electrical property, the discriminator output indicative of the presence and/or the concentration of the gaseous substance.

The method of any clause herein, comprising: determining the presence and/or the concentration of the gaseous substance based at least in part on the discriminator output.

The method of any clause herein, comprising at least one of: causing a monitoring command to a user interface based at least in part on the discriminator output; and causing a control command to a controllable component based at least in part on the discriminator output.

The method of any clause herein, comprising: determining a difference between the discrimination pulse and the simulation pulse in respect of the at least one electrical property, wherein the comparison of the discrimination pulse and the simulation pulse comprises the difference.

The method of any clause herein, wherein the at least one electrical property comprises a voltage.

The method of any clause herein, wherein the gaseous substance comprises at least one of: one or more nitrogen oxides, one or more sulfur oxides, carbon monoxide, carbon dioxide, iodine, hydrogen sulfide, ozone, methane, or water.

The method of any clause herein, wherein the metal organic framework comprises a metal organic framework or an aluminosilicate material.

The method of any clause herein, wherein the method is performed using the sensor discriminator, the gas detection apparatus, the gas-sensor, and/or the gas detection system, of any clause herein.

Although the presently disclosed subject matter has been described with reference to the embodiments illustrated in the attached drawing figures, it is noted that equivalents and/or substitutions may be provided without departing from the scope of the invention defined by the appended claims.

Accordingly, what is claimed as new and desired to be protected by Letters Patent includes the following:

The invention claimed is:

1. A system configured for detecting a presence and/or a concentration of a gaseous substance in a metal organic framework comprising:
   a metal organic framework configured to exhibit at least one electrical property responsive to exposure to a gaseous substance;
   a sensor discriminator for detecting the gaseous substance, the sensor discriminator electrically coupled to the metal organic framework and comprising:
   a power source;
   a discrimination module comprising a comparator; and
   a sensor simulator comprising at least one simulation component,
      wherein the at least one simulation component simulates the metal organic framework under at least one simulation condition;
   at least one processor; and
   at least one memory, the at least one memory comprising a non-transitory computer-readable medium having computer-executable instructions stored thereon, which, when executed by the at least one processor, cause the sensor discriminator to perform operations comprising:
      generating a discrimination pulse,
         wherein the discrimination pulse comprises a first electrical pulse from the power source having passed through the metal organic framework,
      generating a simulation pulse,
         wherein the simulation pulse comprises a second electrical pulse from the power source having passed through the at least one simulation component of the sensor simulator,
      perform, via the comparator of the discrimination module, a comparison of the discrimination pulse to the simulation pulse in respect of at least one electrical property,
         wherein the at least one electrical property depends at least in part on at least one electrical parameter of the metal organic framework augmented by a presence and/or a concentration of the gaseous substance,
      generate, via the discrimination module, a discriminator output comprising the comparison of the discrimination pulse to the simulation pulse and indicative of the presence and/or the concentration of the gaseous substance.

2. The system of claim 1, wherein the sensor discriminator further performs:
   storing the discriminator output on at least one storage device.

3. The system of claim 1, further comprising:
   a timer configured to determine a pulse interval of the discrimination pulse, wherein the timer is electrically coupled to the power source.

4. The system of claim 1, further comprising:
   a location tracking device configured to track a location of the system.

5. The system of claim 1, further comprising:
   a communication interface communicatively coupled to at least one monitoring system, the communication interface configured to transmit the discriminator output to the at least one monitoring system.

6. The system of claim 5, wherein the communication interface comprises a wireless communication device configured to wirelessly communicate with the at least one monitoring system.

7. The system of claim 1, wherein the system is configured to be implemented in association with a combustion system to thereby monitor a concentration of one or more combustion products of the combustion system.

* * * * *